(12) United States Patent
Handa

(10) Patent No.: US 10,393,681 B2
(45) Date of Patent: Aug. 27, 2019

(54) X-RAY TALBOT INTERFEROMETER AND X-RAY TALBOT INTERFEROMETER SYSTEM

(71) Applicant: CANON KABUSHIKI KAISHA, Tokyo (JP)

(72) Inventor: Soichiro Handa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 328 days.

(21) Appl. No.: 15/117,957

(22) PCT Filed: Feb. 12, 2015

(86) PCT No.: PCT/JP2015/054503
§ 371 (c)(1),
(2) Date: Aug. 10, 2016

(87) PCT Pub. No.: WO2015/122542
PCT Pub. Date: Aug. 20, 2015

(65) Prior Publication Data
US 2016/0356730 A1 Dec. 8, 2016

(30) Foreign Application Priority Data
Feb. 14, 2014 (JP) .................. 2014-026677

(51) Int. Cl.
*G21K 1/02* (2006.01)
*G21K 1/06* (2006.01)
(Continued)

(52) U.S. Cl.
CPC ....... *G01N 23/20075* (2013.01); *A61B 6/484* (2013.01); *G21K 1/02* (2013.01); *G21K 1/067* (2013.01); *G21K 2207/005* (2013.01)

(58) Field of Classification Search
CPC .. G01N 23/00; G01N 23/20; G01N 23/20075; G21K 1/00; G21K 1/02;
(Continued)

(56) References Cited

U.S. PATENT DOCUMENTS 5,812,629 A * 9/1998 Clauser ............... A61B 6/032
378/37
2005/0286680 A1* 12/2005 Momose ............... A61B 6/06
378/62
(Continued)

FOREIGN PATENT DOCUMENTS

CN 101257851 A 9/2008
CN 101495853 A 7/2009
(Continued)

OTHER PUBLICATIONS

Surrel, "Moire and Grid Methods: A 'Signal Processing' Approach", Processing of SPIE, Nov. 30, 1994, vol. 2342, pp. 120-127.

*Primary Examiner* — Anastasia Midkiff
(74) *Attorney, Agent, or Firm* — Canon U.S.A., Inc. IP Division

(57) ABSTRACT

The present invention relates to an X-ray Talbot interferometer including a source grating including a plurality of X-ray transmitting portions, configured to allow some of X-rays from an X-ray source to pass therethrough; a beam splitter grating having a periodic structure, configured to diffract X-rays from the X-ray transmitting portions by using the periodic structure to form an interference pattern; and an X-ray detector configured to detect X-rays from the beam splitter grating. The beam splitter grating diffracts an X-ray from each of the plurality of X-ray transmitting portions to form interference patterns each corresponding to one of the plurality of X-ray transmitting portions. The plurality of X-ray transmitting portions are arranged so that the interference patterns, each corresponding to one of the plurality of X-ray transmitting portions, are superimposed on one another to enhance a specific spatial frequency component in a sideband generated by modulation of the interference patterns.

47 Claims, 21 Drawing Sheets

(51) Int. Cl.
*G01N 23/20* (2018.01)
*A61B 6/00* (2006.01)

(58) Field of Classification Search
CPC ...... G21K 1/06; G21K 1/067; G21K 2207/00; G21K 2207/005; A61B 6/00; A61B 6/48; A61B 6/484
See application file for complete search history.

(56) References Cited

U.S. PATENT DOCUMENTS

| | | | |
|---|---|---|---|
| 2009/0092227 A1* | 4/2009 | David | A61B 6/4233 378/36 |
| 2012/0148021 A1* | 6/2012 | Ishii | A61B 6/4233 378/62 |
| 2013/0259194 A1 | 10/2013 | Yip | |

FOREIGN PATENT DOCUMENTS

| | | | |
|---|---|---|---|
| CN | 101873828 A | 10/2010 | |
| CN | 102197302 A | 9/2011 | |
| CN | 102197303 A | 9/2011 | |
| CN | 102413767 A | 4/2012 | |
| CN | 103068310 A | 4/2013 | |
| CN | 103356208 A | 10/2013 | |
| CN | 103364418 A | 10/2013 | |
| CN | 103460251 A | 12/2013 | |
| JP | 4445397 B2 | 4/2010 | |
| JP | 2011-153869 A | 8/2011 | |
| JP | 5162453 B2 | 3/2013 | |
| WO | 2015/102756 A1 | 7/2015 | |

\* cited by examiner

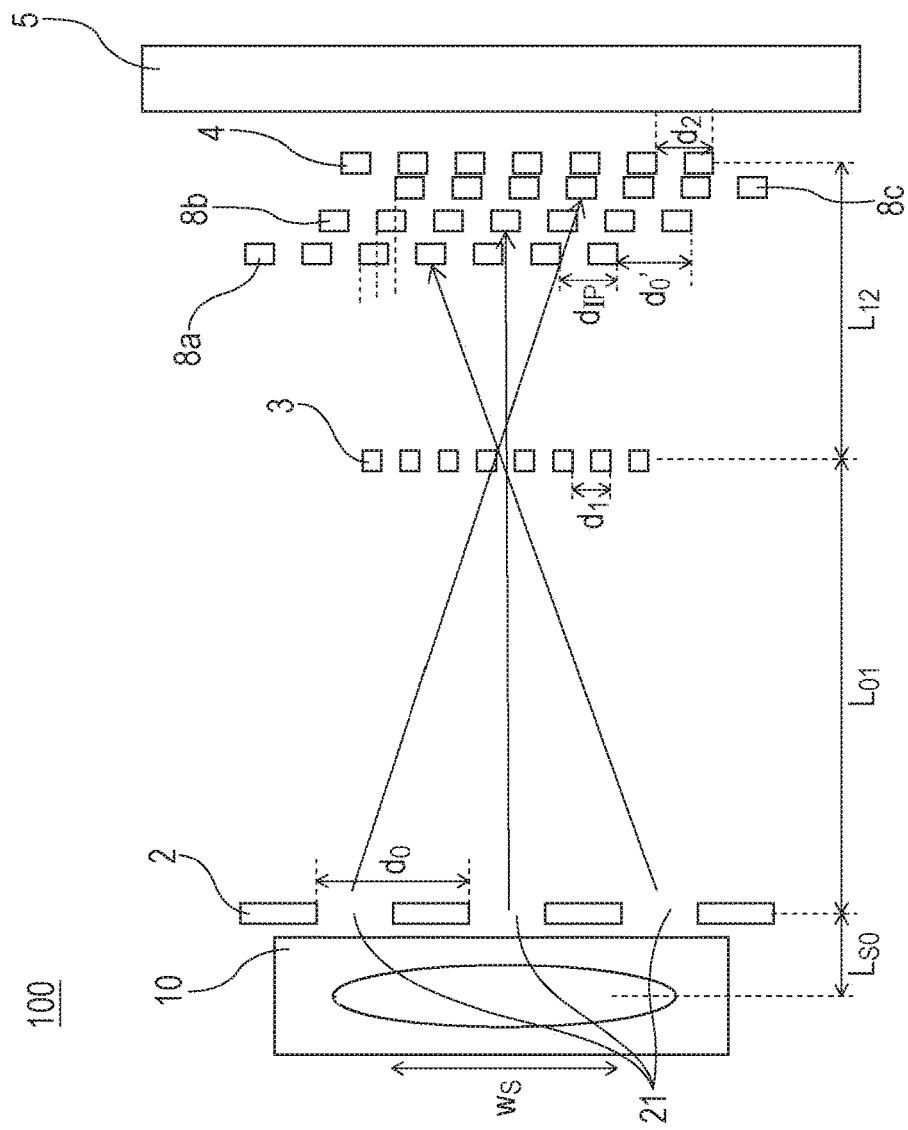

-Prior Art-

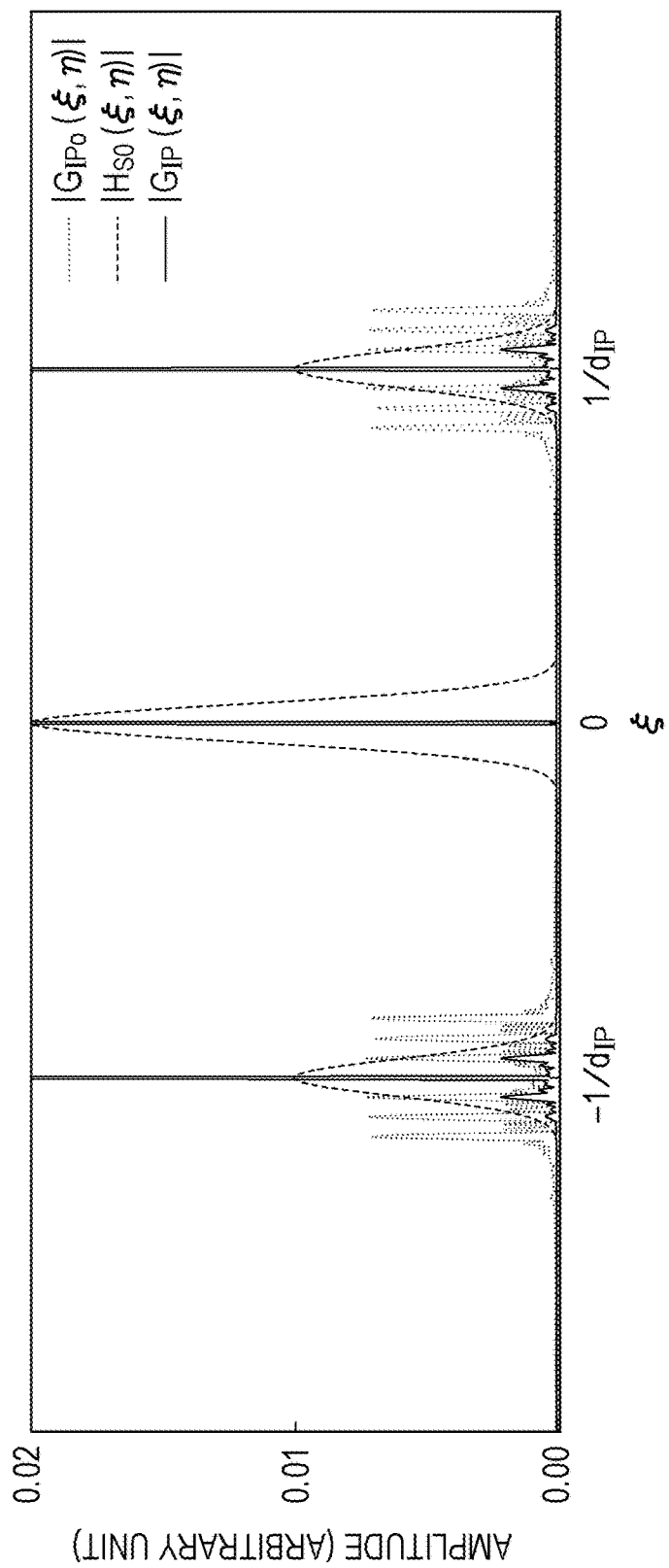

X-RAY TALBOT INTERFEROMETER AND X-RAY TALBOT INTERFEROMETER SYSTEM

TECHNICAL FIELD

The present invention relates to an X-ray Talbot interferometer and an X-ray Talbot interferometer system.

BACKGROUND ART

An X-ray phase imaging method is an imaging method which utilizes the phase change induced by a sample as X-rays traverse the sample. One of the several X-ray phase imaging methods proposed in the related art is Talbot interferometry described in, for example, Patent Literature reference 1 (PTL 1).

A Talbot interferometer generally includes two or three gratings each having a periodic structure. Among the gratings, a grating which is generally placed near the sample may be referred to as a "beam splitter grating", a grating which is generally placed near an X-ray detector may be referred to as an "analyzer grating", and a grating which is generally placed near an X-ray source may be referred to as a "source grating". Each of the gratings described above may be a grating having a one-dimensional periodic pattern or a grating having a two-dimensional pattern. The X-ray detector used is generally a detector capable of measuring a two-dimensional intensity distribution of X-rays incident on a detection surface of the X-ray detector.

The beam splitter grating is typically a phase-modulation transmission-based diffraction grating. X-rays incident on the beam splitter grating are diffracted by the periodic structure of the grating, forming an interference pattern (also referred to as a "self-image of the grating") at a predetermined position due to the so-called Talbot effect. The interference pattern reflects, for example, changes in the phase of propagating X-rays as they traverse the sample and deforms. By performing measurement and analysis of the intensity distribution of the interference pattern, information on the shape and internal structure of the sample may be obtained. In the present invention and throughout the specification, any method for acquiring information on the sample by utilizing X-ray phase changes induced by the sample is referred to as an X-ray phase contrast imaging method even if the information is not converted into an image.

The analyzer grating is typically a grating in which X-ray transmitting portions and X-ray shielding portions are periodically arrayed and thereby having a periodic transmittance distribution. The analyzer grating is placed at the position where the interference pattern described above occurs, and is thus used in order to cause a moiré pattern to appear in the intensity distribution of the X-rays that have passed through the grating. The moiré pattern reflects the deformation of the interference pattern, and the period of the moiré pattern can be increased without limitation. Thus, even if the spatial resolution of the detector used is not high enough to ensure that the interference pattern can be directly detected, detection of a moiré pattern with a large period will enable indirect obtaining of the information on the interference pattern. A Talbot interferometer that utilizes the occurrence of a moiré pattern between the interference pattern and the grating is described in, for example, PTL 1.

As described above, the analyzer grating is used to compensate for insufficient spatial resolution of the X-ray detector. Thus, when a detector having a sufficiently high spatial resolution is used, the use of the analyzer grating is not essential. Since the interference pattern generally has a period of approximately several micrometers (μm), and is too fine to be directly detected with a typical X-ray detector, it is common to use the analyzer grating.

Similarly to the typical analyzer grating, the source grating is also a grating having a structure in which X-ray transmitting portions and X-ray shielding portions are periodically arrayed. The source grating is generally placed near an X-ray emission spot inside the X-ray source (X-ray generator), and is thus used in order to form an array of virtual linear light emitting portions (in a two-dimensional grating, a minute light emitting spots). X-rays emitted from the individual linear light emitting portions formed in the manner described above form a plurality of interference patterns, each described above, and the interference patterns are superimposed on one another while displaced by an integer, said integer being a multiple of the pattern period when no sample or the like is placed in X-ray paths. Accordingly, a periodic pattern having a high X-ray intensity and high fringe visibility can be formed. To achieve such superposition of interference patterns as described above, it is desirable to design each grating so that its grating period and a distance between gratings satisfy predetermined conditions. A Talbot interferometer that uses such a source grating as described above may be particularly referred to as a "Talbot-Lau interferometer". A Talbot interferometer that uses such a source grating is described in, for example, Patent Literature reference 2 (PTL 2). Hereinafter, the term "Talbot interferometer" is used to also include a Talbot-Lau interferometer.

Using the source grating makes it possible to use an X-ray source having a comparatively large light emitting spot size. If the light emitting spot size is small enough to directly form a high-visibility interference pattern, the use of the source grating is not essential. However, the formation of such a minute light emitting spot in an X-ray tube, which is the most common X-ray source, results in a tendency for the X-ray output per unit time to decrease and the imaging time to significantly increase. Thus, a source grating is generally used when an X-ray tube is used as the X-ray source.

In a Talbot interferometer, it is common to acquire an X-ray transmittance distribution of the sample that is an image based on a principle similar to that of standard X-ray imaging (absorption contrast imaging), and also acquire information on a fringe phase distribution of the interference pattern and a visibility distribution of the interference pattern. In general, the fringe phase and visibility of the interference pattern respectively mainly reflect the spatial differentiation of the phase distribution of the X-rays that have propagated through the sample and the degree of X-ray small-angle scattering caused by fine particles, a fibrous structure, edge portions of an object, or the like.

CITATION LIST

Patent Literature

PTL 1 Japanese Patent No. 4445397
PTL 2 Japanese Patent No. 5162453

SUMMARY OF INVENTION

An aspect of the present invention provides an X-ray Talbot interferometer which includes: a source grating including a plurality of X-ray transmitting portions, and configured to allow some of X-rays from an X-ray source to pass therethrough; a beam splitter grating having a periodic structure, and configured to diffract X-rays from the X-ray transmitting portions by using the periodic structure to form an interference pattern; and an X-ray detector configured to detect X-rays from the beam splitter grating. The beam splitter grating diffracts an X-ray from each of the plurality of X-ray transmitting portions by using the periodic structure to form interference patterns each corresponding to one of the plurality of X-ray transmitting portions. The plurality of X-ray transmitting portions are arranged so that the interference patterns, each corresponding to one of the plurality of X-ray transmitting portions, are superimposed on one another to enhance a specific spatial frequency component. The specific spatial frequency component is a spatial frequency component in a sideband generated by modulation of spatial frequency components specific to the interference patterns by a sample.

Further features of the present invention will become apparent from the following description of exemplary embodiments with reference to the attached drawings.

BRIEF DESCRIPTION OF DRAWINGS

FIG. 1 is a schematic diagram of an X-ray Talbot interferometer according to a first embodiment.

FIGS. 4A-1, 4A-2, 4B-1, and 4B-2 illustrate an example of pieces of sample information in the first embodiment.

FIGS. 5A-1, 5A-2, 5B-1, and 5B-2 illustrate an example of pieces of sample information in the first embodiment.

FIG. 7 illustrates an example of spectra of an interference pattern obtained in Comparative Example 1.

FIGS. 8A-1, 8A-2, 8B-1, and 8B-2 illustrate an example of pieces of sample information in Comparative Example 1.

DESCRIPTION OF EMBODIMENTS

Figure 2A:
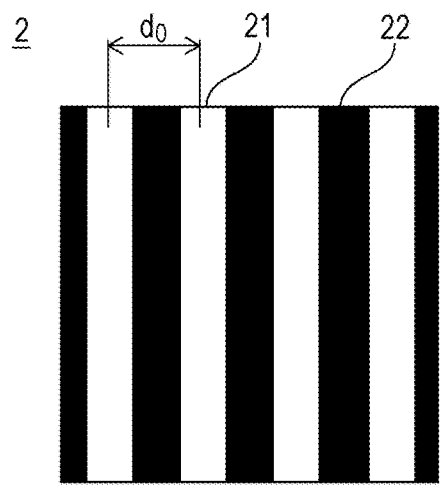
FIGS. 2A, 2B, and 2C are diagrams illustrating grating patterns according to first and second embodiments.

With the use of a source grating, a Talbot-Lau interferometer is capable of forming a periodic pattern having comparatively high visibility even when including an X-ray source having a large light emitting spot size. However, the use of the X-ray source having a large light emitting spot size increases the number of interference patterns to be superimposed with the positions thereof being displaced from each other (by an amount corresponding to one period of the periodic patterns). This may result in, due to the geometric unsharpness effect, a reduction in the spatial resolution at which a sample image can be acquired, for the following reason: X-rays from different transmitting portions in the source grating are incident on the same position on the sample, thereby forming interference patterns at different positions.

With the use of the analyzer grating, the Talbot interferometer is capable of indirectly obtaining information on an interference pattern by utilizing the moiré effect even when including an X-ray detector that does not have a high spatial resolution enough to detect an interference pattern. However, sample information is affected by the modulation transfer function of the detector in a similar way to that for standard X-ray imaging, and a sufficient spatial resolution to acquire a sample image may not necessarily be achieved.

In a first embodiment, a description will be given of a Talbot interferometer and a Talbot interferometer system having a higher spatial resolution than those of the related art even when including an X-ray source having the same light emitting spot size as that of the Talbot interferometer of the related art. In a second embodiment, a description will be given of a Talbot interferometer and a Talbot interferometer system having a higher spatial resolution than those of the related art even when including the same X-ray detector as that of the Talbot interferometer of the related art.

According to the first embodiment, it may be possible to provide a Talbot interferometer and a Talbot interferometer system having a higher spatial resolution than those of the related art even when including an X-ray source having the same light emitting spot size as that of the Talbot interferometer of the related art.

According to the second embodiment, it may be possible to provide a Talbot interferometer and a Talbot interferometer system having a higher spatial resolution than those of the related art even when including the same X-ray detector as that of the Talbot interferometer of the related art.

Preferred embodiments of the present invention will be described in detail hereinafter with reference to the accompanying drawings. In the drawings, the same or substantially the same components are assigned the same reference numerals, and are not redundantly described.

First Embodiment

This embodiment provides an X-ray Talbot-Lau interferometer (hereinafter also referred to simply as an "interferometer") including a source grating, of which the frequency components deviated from the carrier of the interference pattern are enhanced.

In a Talbot-Lau interferometer of the related art, a source grating is configured to enhance the carrier of the interference pattern. In other words, the interferometer of the related art is configured to superimpose interference patterns, which are formed by individual minute X-ray sources in a virtual X-ray source array formed in the source grating, on one another so that bright portions of the interference patterns overlap and dark portions of the interference patterns overlap to increase contrast. In contrast, an interferometer according to this embodiment is configured such that bright portions of interference patterns partially overlap and dark portions of the interference patterns partially overlap. A more detailed description will be given hereinbelow.

Figure 6:
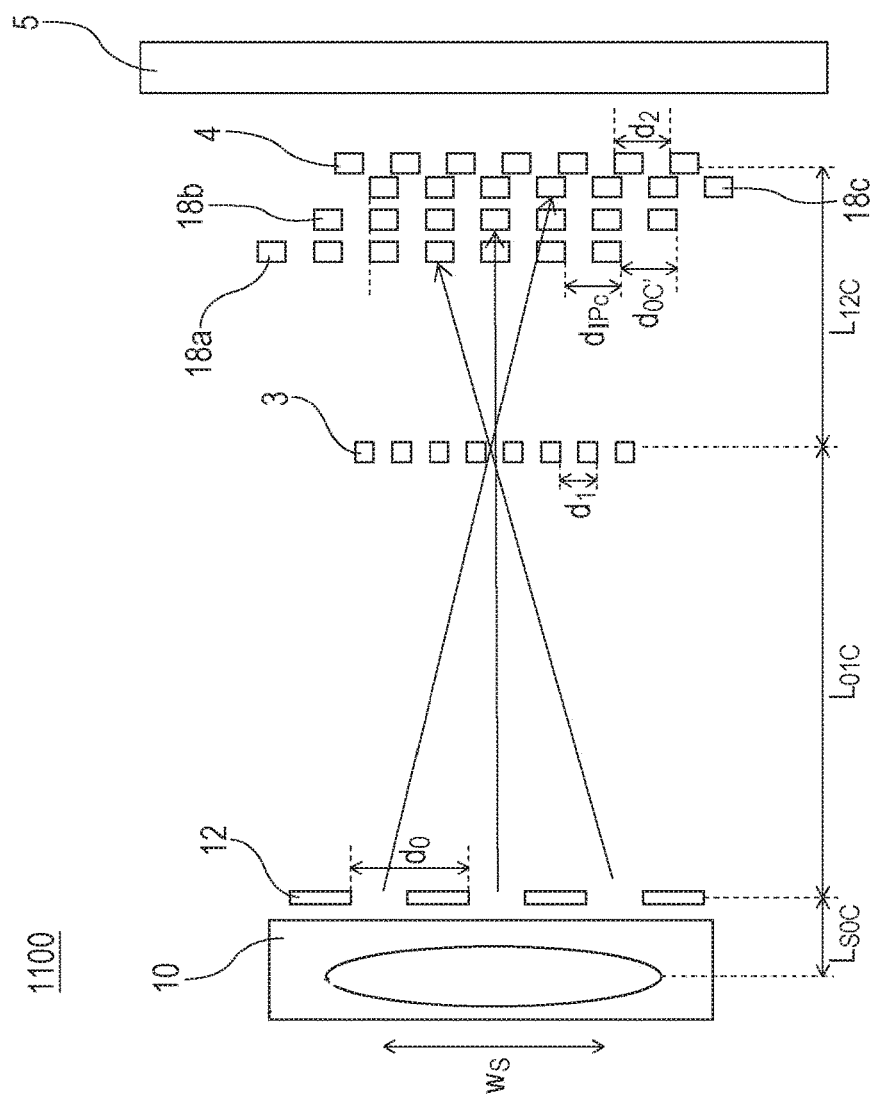
FIG. 6 is a schematic diagram of an X-ray Talbot interferometer according to Comparative Example 1.

FIG. 6 is a schematic diagram of an X-ray Talbot-Lau interferometer 1100 according to Comparative Example 1, which is an X-ray Talbot-Lau interferometer of the related art. The X-ray Talbot interferometer 1100 includes an X-ray source 10, a source grating 12, a beam splitter grating 3, an analyzer grating 4, and an X-ray detector 5. Although not illustrated in FIG. 6, when imaged, a sample is arranged near the beam splitter grating 3. The sample may be arranged upstream of the beam splitter grating 3 (between the source grating 12 and the beam splitter grating 3), or downstream of the beam splitter grating 3 (between the beam splitter grating 3 and the analyzer grating 4).

As described previously, in the X-ray Talbot-Lau interferometer of the related art, interference patterns 18a, 18b, and 18c formed by X-rays emitted from individual X-ray transmitting portions in the source grating 12 while no sample or the like is placed in X-ray paths extending from the source grating 12 to the X-ray detector 5 are superimposed on one another while displaced exactly by an amount corresponding to a pattern period $d_{IPc}$. That is, the relative amount of displacement $d_{0C}'$ by which a plurality of interference patterns are superimposed on one another is equal to the pattern period $d_{IPc}$. Thus, the interference patterns formed by the X-rays from the individual transmitting portions are superimposed so that bright portions of the interference patterns are accurately overlapped with each other and dark portions of the interference patterns are accurately overlapped with each other. Accordingly, a high-intensity periodic pattern (a periodic pattern formed by superposition of the plurality of interference patterns) having visibility similar to that of an interference pattern formed by an X-ray from a single transmitting portion can be formed on the analyzer grating. Even if interference patterns formed by the X-rays from the respective transmitting portions are superimposed on one another while displaced by an integer multiple of the pattern period, the interference patterns are superimposed in such a manner that the bright portions of the interference patterns are accurately overlapped with each other and the dark portions of the interference patterns are accurately overlapped with each other. Thus, the amount of displacement between the interference patterns may be equal to an integer multiple of the pattern period.

In order to ensure that interference patterns formed by the X-rays from the individual transmitting portions in the source grating are superimposed on one another while displaced exactly by an amount equal to the pattern period or an amount equal to an integer multiple of the pattern period, the source grating may have a grating period $d_{0C}$ which is given by

[Math. 1]

$$d_{0c} = n_1 \times d_{Ipc} \times \frac{L_{01c}}{L_{12c}},$$

where $n_1$ is a positive integer, $L_{01C}$ denotes the distance between the source grating and the beam splitter grating, and $L_{12C}$ denotes the distance between the beam splitter grating and the analyzer grating. Note that the distance between elements is the distance between the centers of the elements. The value $n_1$ indicates the number of pattern periods by which the interference patterns are superimposed on one another while displaced. When $n_1=1$, the interference patterns are superimposed on one another while displaced by an amount equal to the pattern period, as indicated by the interference patterns 18a, 18b, and 18c illustrated in FIG. 6.

Figures 1, 4A:
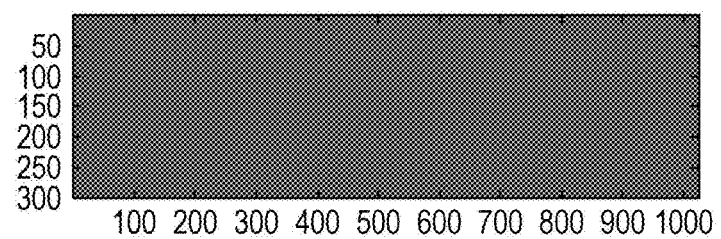

In an X-ray Talbot interferometer 100 according to this embodiment, in contrast, as illustrated in FIG. 1, interference patterns 8a, 8b, and 8c formed by X-rays from individual transmitting portions in a source grating 2 are superimposed on one another while displaced by a distance that is different from a pattern period $d_{IP}$ which is obtained when no sample is placed. That is, in the Talbot interferometer 100 according to this embodiment, an amount of displacement $d_0'$ by which the interference patterns 8a, 8b, and 8c formed by the X-rays from the individual transmitting portions are displaced is not equal to the interference pattern period $d_{IP}$. Bright portions of the interference patterns 8a, 8b, and 8c, which are formed by the X-rays from individual openings, overlap each other with a displacement therebetween instead of being accurately overlapped with each other, and dark portions of the interference patterns 8a, 8b, and 8c overlap each other with a displacement therebetween instead of being accurately overlapped with each other. The source grating 2 has a grating period $d_0$ which can be represented by

[Math. 2]

$$d_0 = n_1 \times d_{Ip} \times \frac{L_{01}}{L_{12}}(1 + \alpha_1) \quad (1)$$

by using the rate of deviation $\alpha_1$ from the condition in which the interference patterns 8a, 8b, and 8c are accurately overlapped with each other, where $L_{01}$ denotes the distance between the source grating and the beam splitter grating, and $L_{12}$ denotes the distance between the beam splitter grating and the analyzer grating. The rate of deviation $\alpha_1$ may also take a negative value, where $\alpha_1 \neq 0$. When $\alpha_1$ is equal to 0, the design conditions of the source grating are the same as those in Comparative Example 1. Furthermore, in a typical Talbot-Lau interferometer, the amount of displacement between interference patterns may be an integer multiple of 2 or more of the pattern period. Likewise, the Talbot-Lau interferometer according to this embodiment may also be designed such that the amount of displacement between interference patterns is an integer multiple of 2 or more of the pattern period with a certain rate of deviation. However, such a design (that $n_1$ is an integer greater than or equal to 2) has a drawback in that the overall X-ray transmittance of the source grating is reduced, which is generally not preferable. The following description focuses on the case where $n_1=1$. In a case where the X-ray Talbot interferometer does not include an analyzer grating between the beam splitter grating and the X-ray detector, the distances $L_{12C}$ and $L_{12}$ may denote the distance between the beam splitter grating and the detection surface of the X-ray detector.

In FIG. 1 and FIG. 6, the interference patterns 8a to 8c and 18a to 18c formed by the X-rays from the individual transmitting portions are depicted at different positions also in the lateral direction in FIG. 1 and FIG. 6, for convenience of illustration. Actually, however, the interference patterns 8a to 8c and 18a to 18c are formed on the analyzer grating 4 (or on the detection surface of the X-ray detector if the analyzer grating 4 is not included). That is, the distance between each of the source gratings 2 and 12 and the interference pattern 8a is equal to the distance between each of the source gratings 2 and 12 and the interference pattern 8b.

This embodiment will be described in more detail hereinafter.

FIG. 1 is a schematic diagram of the X-ray Talbot interferometer (hereinafter also referred to simply as the "interferometer") 100 according to this embodiment. The interferometer 100 includes the source grating 2 and the beam splitter grating 3. The source grating 2 has X-ray transmitting portions, and is configured to allow some of X-rays emitted from an X-ray source 10 to pass therethrough. The beam splitter grating 3 diffracts X-rays from the X-ray transmitting portions in the source grating 2 by using the periodic structure to form the interference patterns 8a to 8c each corresponding to one of the X-ray transmitting portions. The interferometer 100 further includes the analyzer grating 4 and the X-ray detector 5. The analyzer grating 4 blocks some of the X-rays which form the interference patterns 8a to 8c. The X-ray detector 5 detects the intensity of the X-ray from the beam splitter grating 3. The interferometer 100 can constitute an X-ray Talbot interferometer system with a sample information acquisition unit (which may be an arithmetic unit comprising a processor and a storage device, or the like) configured to acquire information on a sample by using information relating to a result of detection performed by the X-ray detector 5.

As described above, the analyzer grating 4 is not essential when the X-ray detector 5 has a high spatial resolution enough to detect an interference pattern. In the present invention and throughout the specification, the term "detecting X-rays from the beam splitter grating" is used to also include detecting X-rays incident on an optical element, the sample, and the like after they are incident on the beam splitter grating. That is, the detection of X-rays from the analyzer grating 4 is also referred to as the detection of the intensity of X-rays from the beam splitter grating 3 if the X-rays are X-rays that have propagated through the beam splitter grating 3. In the example illustrated in FIG. 1, the X-ray source 10, which irradiates the source grating 2 with X-rays, and the three gratings 2 to 4 and the detector 5, described above, constitute the X-ray Talbot interferometer 100. Alternatively, the X-ray source 10 may be separate from the Talbot interferometer 100, and the X-ray source 10 and the Talbot interferometer 100 may be used in combination. In the present invention and throughout the specification, what is simply referred to as a "Talbot interferometer" includes both a Talbot interferometer including an X-ray source and a Talbot interferometer including no X-ray source (the Talbot interferometer may have a space for installing an X-ray source).

Figure 2B:
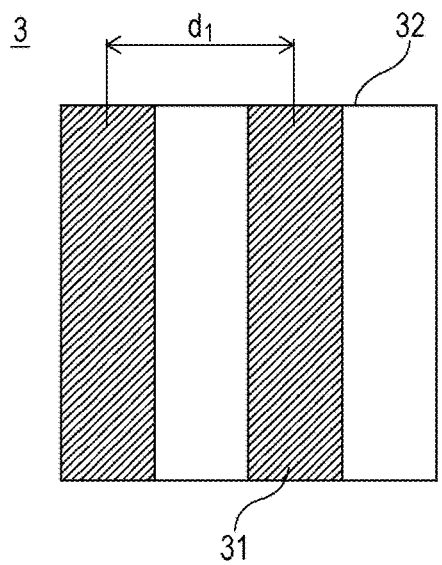
Figure 2C:
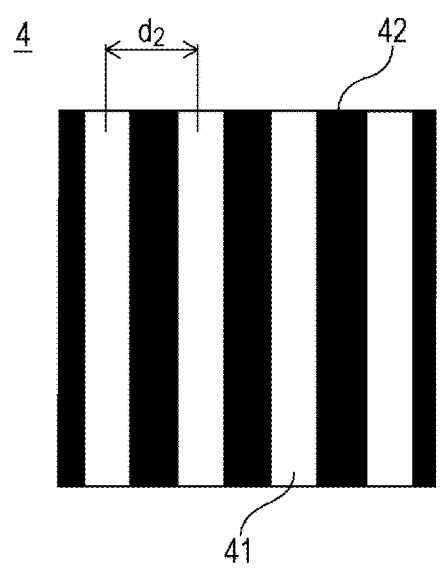

FIGS. 2A, 2B, and 2C illustrate example patterns of the respective gratings. FIGS. 2A, 2B, and 2C illustrate the pattern of the source grating 2, the pattern of the beam splitter grating 3, and the pattern of the analyzer grating 4, respectively. The source grating 2 has a one-dimensional periodic structure in which X-ray transmitting portions (also referred to as opening portions) 21 with high X-ray transmittance and X-ray shielding portions 22 with low X-ray transmittance are arrayed in one direction. The beam splitter grating 3 is a phase-modulation diffraction grating having a one-dimensional periodic structure in which phase-advancing portions 31 and phase-delaying portions 32 are arrayed in one direction. The specific pattern and the amount of phase modulation of the beam splitter grating 3 may be selected from among various patterns suitable for generally accepted Talbot interferometers, and are not particularly limited here. The analyzer grating 4 has a one-dimensional periodic structure in which X-ray transmitting portions 41 with high X-ray transmittance and X-ray shielding portions 42 with low X-ray transmittance are arrayed in one direction.

The illustrated grating patterns are examples, and, for example, each grating may have a two-dimensional periodic structure. Further, the phase difference between X-rays that have passed through the phase-advancing portions 31 and X-rays that have passed through the phase-delaying portions 32 is not particularly limited. A beam splitter grating having a phase difference of $\pi$ rad or $\pi/2$ rad is generally used, or a beam splitter grating having a phase difference that takes any other value may also be used.

Similarly to the Talbot-Lau interferometer of the related art, the values of the distances $L_{01}$ and $L_{12}$ preferably satisfy the condition in which interference pattern visibility is particularly high on the analyzer grating 4 if the Talbot effect produced when X-rays from the individual virtual linear light emitting portions formed by the source grating 2 are diffracted by the beam splitter grating 3 is taken into account.

In the following, the effect produced when interference patterns formed by X-rays from the individual virtual linear light emitting portions are superimposed on one another with a displacement which is not equal to the pattern period (i.e., the effect yielded when the rate of deviation $\alpha_1$ is not 0) in this embodiment will be described with a simple model.

First, the coordinate system (x, y) is taken on the analyzer grating, and the periodic direction of the interference patterns is assumed to coincide with the x-axis direction. In this case, an intensity distribution $g_{IPo}(x, y)$ of an interference pattern on the analyzer grating which is formed by X-rays originating from a single point on the source grating can be expressed by

[Math. 3]

$$g_{IPo}(x, y) = a(x, y) + b(x, y)\cos\left[\frac{2\pi}{d_{Ip}}x + \phi(x, y)\right], \quad (2)$$

where a(x, y) denotes the distribution of average intensities of the interference pattern that reflect the X-ray transmittance distribution of the sample, and b(x, y) denotes the amplitude distribution of the interference pattern that reflects the X-ray transmittance distribution of the sample and the X-ray small-angle scattering power distribution in the periodic direction of the interference pattern. In addition, $\phi(x, y)$ denotes the phase distribution of the interference pattern that reflects the distribution obtained by differentiation of the phase distribution (wavefront shape) of X-rays that have propagated through the sample in the periodic direction of the interference pattern. In this case, the spatial frequency component specific to the interference pattern in this embodiment is a spatial frequency component whose periodic direction is the x-axis direction and whose spatial frequency is given by $1/d_{IP}$. The spatial frequency component specific to the interference pattern can also be regarded as being amplitude-modulated and phase-modulated by sample information, namely, b(x, y) and $\phi(x, y)$. Throughout the specification, the spatial frequency component specific to the interference pattern modulated by the sample information may be referred to as the carrier. It may be possible that the harmonic component instead of the fundamental component of the interference pattern is used as the carrier. However, the harmonic component of the interference pattern is generally much smaller than the fundamental component, and is thus seldom used as the carrier. Given that

[Math. 4]

$$c(x,y)=b(x,y)e^{iP(x,y)}, \quad (3)$$

Expression (2) can be rewritten as

[Math. 5]

$$g_{IPo}(x, y) = a(x, y) + \frac{1}{2}c(x, y)e^{i\frac{2\pi}{d_{Ip}}x} + \frac{1}{2}c^*(x, y)e^{-i\frac{2\pi}{d_{Ip}}x}, \quad (4)$$

where * represents complex conjugate. Applying the two-dimensional Fourier transform to both sides yields

[Math. 6]

$$G_{Ipo}(\xi, \eta) = A(\xi, \eta) + \frac{1}{2}C\left(\xi - \frac{1}{d_{Ip}}, \eta\right) + \frac{1}{2}C^*\left(\xi + \frac{1}{d_{Ip}}, \eta\right), \quad (5)$$

where capital letters represent the Fourier transform of the functions (the same applies to the following), $\xi$ represents the spatial frequency in the x-axis direction, and $\eta$ represents the spatial frequency in the y-axis direction.

Next, consideration will be given to the X-ray intensity distribution on the analyzer grating which is obtained when an X-ray emission spot having a spatial spread and the presence of a source grating are taken into consideration. The sample and the beam splitter grating are approximated as being in the same position. Further, the X-ray emission spot and the source grating are approximated as being in the same position.

The function representing the shape of the light emission intensity distribution of the X-ray emission spot for the x-axis and y-axis position coordinates $(x_0, y_0)$ of the position of the X-ray emission spot and the source grating is represented by $g_S(x_0, y_0)$. Further, the transmittance distribution of the source grating is represented by $t_0(x_0, y_0)$. In this case, the effective light emission intensity distribution $g_{SO}(x_0, y_0)$ of the X-ray emission spot can be expressed by

[Math. 7]

$$g_{SO}(x_0,y_0)=g_S(x_0,y_0)t_0(x_0,y_0). \quad (6)$$

In this case, furthermore, the X-ray intensity distribution $g_{IP}(x, y)$ on the analyzer grating can be approximately expressed by the equation below as a convolution of $g_{IPo}(x, y)$ and the point spread function $h_{SO}(x, y)$ representing blurring caused by the effective light emission intensity distribution of the X-ray emission spot

[Math. 8]

$$g_{IP}(x,y)=g_{IPo}(x,y)*h_{SO}(x,y), \quad (7)$$

where * represents convolution. Unlike $g_{IPo}(x, y)$, $g_{IP}(x, y)$ represents an intensity distribution of an interference pattern actually formed on the analyzer grating (that is, an interference pattern formed by all of the X-rays that have passed through the source grating).

Further, $h_{SO}(x, y)$ can be expressed by

[Math. 9]

$$h_{SO}(x, y) \propto g_{SO}\left(-\frac{L_{01}}{L_{12}}x, -\frac{L_{01}}{L_{12}}y\right), \quad (8)$$

where $h_S(x, y)$ is a function that represents

[Math. 10]

$$h_s(x, y) \propto g_s\left(-\frac{L_{01}}{L_{12}}x, -\frac{L_{01}}{L_{12}}y\right). \quad (9)$$

Note that $h_S(x, y)$ is the point spread function described above which is obtained when no source grating is included.

Further, when the source grating has a simple sinusoidal transmittance distribution, $t_0(x_0, y_0)$ can be expressed by

[Math. 11]

$$t_0(x_0, y_0) = 1 + \cos\left(\frac{2\pi}{d_0}x_0\right). \quad (10)$$

Further, the relative amount of displacement $d_0'$ between interference patterns can be expressed by the following equation using the pitch $d_0$ of the source grating and the geometry ($L_{12}$ and $L_{01}$) of the interferometer:

[Math. 12]

$$d_0' = d_0\frac{L_{12}}{L_{01}}. \quad (11)$$

In this case, Expression (8) can be rewritten as

[Math. 13]

$$h_{SO}(x, y) = h_s(x, y)\left[1 + \cos\left(\frac{2\pi}{d_0'}x\right)\right]. \quad (12)$$

$g_{IP}(x, y)$ can also be regarded as an intensity distribution produced as a result of superimposing a plurality of interference patterns formed by the X-rays from a plurality of X-ray transmitting portions in the source grating. In this case, $H_{SO}(\xi, \eta)$, which is the Fourier transform of $h_{SO}(x, y)$, is given by

[Math. 14]

$$H_{SO}(\xi, \eta) = H_s(\xi, \eta) + \frac{1}{2}H_s\left(\xi - \frac{1}{d_0'}, \eta\right) + \frac{1}{2}H_s\left(\xi + \frac{1}{d_0'}, \eta\right). \quad (15)$$

Accordingly, using Expressions (5), (7), and (13) and the convolution theorem, $G_{IP}(\xi, \eta)$, which is the Fourier transform of $g_{IP}(x, y)$, can be expressed by

[Math. 15]

$$G_{Ip}(\xi, \eta) = G_{Ipo}(\xi, \eta)H_{s0}(\xi, \eta) \approx A(\xi, \eta)H_s(\xi, \eta) + \frac{1}{4}C\left(\xi - \frac{1}{d_{Ip}}, \eta\right)H_s\left(\xi - \frac{1}{d_0'}, \eta\right) + \frac{1}{4}C^*\left(\xi + \frac{1}{d_{Ip}}, \eta\right)H_s\left(\xi + \frac{1}{d_0'}, \eta\right). \quad (14)$$

It is assumed here that the rates of spatial change in $a(x, y)$, $b(x, y)$, $\phi(x, y)$, and $h_S(x, y)$ are sufficiently moderate compared to $d_{IP}$ and $d_0'$.

As is seen from Expression (14), sample information $c(x, y)$ is filtered by a frequency filter $H_S$ during the transmission of the information due to the effect of the source grating and the X-ray emission spot having a spatial spread. As is also seen, the shape of the filter $H_S$ is determined by the light emission intensity distribution of the X-ray emission spot and the distances $L_{01}$ and $L_{12}$, and the relative position of the filter $H_S$ with respect to $C(\xi, \eta)$ is determined by the period $d_{IP}$ of the interference fringes, the grating period $d_0$ of the source grating, and the distances $L_{01}$ and $L_{12}$.

Next, consideration will be given to an X-ray intensity distribution which is finally measured when X-rays pass through the analyzer grating and enter the X-ray detector. A transmittance distribution $t_2(x, y)$ of the analyzer grating is represented by

[Math. 16]

$$t_2(x, y) = 1 + \cos\left(\frac{2\pi}{d_2}x - \phi_r\right), \quad (15)$$

where $d_2$ denotes the grating period of the analyzer grating, and $\phi_r$ denotes the phase of the analyzer grating (corresponding to the x-direction position of the grating). Similarly to the source grating, the grating period $d_2$ of the analyzer grating can also take an integer multiple of 2 or more of $d_{IP}$ or take a value close to it, which is also not preferable in general because the X-ray transmittance will be reduced. In the following, a description will be given of the case where the grating period $d_2$ has a value close to $d_{IP}$. Further, since the analyzer grating is generally placed in close vicinity of the detection surface of the X-ray detector, the analyzer grating and the detection surface are approximated as being in the same position. In this case, if the point spread function (PSF) specific to intensity distribution measurement performed by the X-ray detector used is represented by $h_D(x, y)$, the X-ray intensity distribution $g_M(x, y)$, which is finally measured, can be expressed by the following equation using the intensity distribution $(g_{IP}(x, y)t_2(x, y))$ of X-rays that have passed through the analyzer grating and the point spread function of the detector:

[Math. 17]

$$g_M(x,y) = [g_{IP}(x,y)t_2(x,y)]*h_D(x,y). \quad (16)$$

Accordingly, $G_M(\xi, \eta)$, which is the Fourier transform of $g_M(x, y)$, can be expressed by

[Math. 18]

$$G_M(\xi, \eta) = [G_{Ip}(\xi, \eta) * T_2(\xi, \eta)]H_D(\xi, \eta) \approx \Big[ A(\xi, \eta)H_s(\xi, \eta) + \frac{1}{8}C\left(\xi - \frac{1}{d_{Ip}} + \frac{1}{d_2}, \eta\right)H_s\left(\xi - \frac{1}{d_0'} + \frac{1}{d_2}, \eta\right)e^{i\phi_r} + \frac{1}{8}C^*\left(\xi + \frac{1}{d_{Ip}} - \frac{1}{d_2}, \eta\right)H_s\left(\xi + \frac{1}{d_0'} - \frac{1}{d_2}, \eta\right)e^{-i\phi_r} \Big] H_D(\xi, \eta). \quad (17)$$

Here, a term in which the center of the function is located in a region that is very far from the origin in the $(\xi, \eta)$ space is considered to have a sufficiently small value when filtered with $H_D(\xi, \eta)$, and is ignored. Further, $|H_D(\xi, \eta)|$ is a function corresponding to the modulation transfer function (MTF) of the detector.

In one of the cases where the interferometer is being used, the analyzer grating is moved along the x axis so that intensity distribution measurement can be performed a plurality of times with $\phi_r$ changed in order to acquire information on the sample. In this case, the X-ray detector performs detection before and after the moving unit causes a movement of the relative position to acquire a plurality of detection results at different relative positions of the analyzer grating with respect to the interference pattern. The information obtained as a result of intensity distribution measurement performed a plurality of times is subjected to predetermined computation based on the principle of the so-called phase shift method, so that spectra for the three terms in brackets in Expression (17) can be separately calculated. For example, intensity distribution measurement is performed three times, and information on the intensity distribution $g_M(x, y, k)$ and its Fourier transform, that is, $G_M(\xi, \eta, k)$ (where k=1, 2, 3), is obtained. In this case, if $\phi_r$ is changed in the manner given by

[Math. 19]

$$\phi_r(k) = 0, \frac{2\pi}{3}, \frac{4\pi}{3} (k = 1, 2, 3), \quad (18)$$

then, restored values (which refer to the values actually acquired from the measurement results) $A_R(\xi, \eta)$ and $C_R(\xi, \eta)$ of $A(\xi, \eta)$ and $C(\xi, \eta)$, which are sample information expressed in the frequency domain, can be calculated by

[Math. 20]

$$A_R(\xi, \eta) = \frac{1}{3}\sum_{k=1}^{3} G_M(\xi, \eta, k) \quad (19)$$
$$= A(\xi, \eta)H_s(\xi, \eta)H_D(\xi, \eta)$$

and

[Math. 21]

$$C_R(\xi, \eta) = \frac{1}{3}\sum_{k=1}^{3} G_M\left(\xi + \frac{1}{d_{IP}} - \frac{1}{d_2}, \eta, k\right)e^{-i\frac{2\pi}{3}(k-1)} \quad (20)$$
$$= \frac{1}{8}C(\xi, \eta)H_s(\xi - \xi_0, \eta)H_D(\xi - \xi_2, \eta),$$

respectively, where $\xi_0$ and $\xi_2$ are given by

[Math. 22]

$$\xi_0 = \frac{1}{d_0'} - \frac{1}{d_{IP}} \quad (21)$$

and

[Math. 23]

$$\xi_2 = \frac{1}{d_2} - \frac{1}{d_{IP}}, \quad (22)$$

respectively.

As is seen from Expressions (19) and (20), the sample information restored by the above-described technique is finally influenced by two frequency filters, namely, $H_S$ and $H_D$, which are the Fourier transform of the point spread functions of the X-ray source and the X-ray detector, respectively. As is also seen from Expression (19), $A_R(\xi, \eta)$ (and $a_R(x, y)$, which is expressed in the (x, y) space), which is acquired, is not affected by the grating periods of the source grating and the analyzer grating since the center position of $A(\xi, \eta)$, which is the spectrum of sample information, and the center positions of the two frequency filters to be applied to $A(\xi, \eta)$ always match.

As is seen from Expression (20), in contrast, for $C_R(\xi, \eta)$ (and $c_R(x, y)$, which is expressed in the (x, y) space), which is acquired, the center position of $C(\xi, \eta)$, which is the spectrum of sample information, and the center positions of the two frequency filters to be applied to $C(\xi, \eta)$ do not always match. The relative amounts of displacement of the filters are determined in accordance with the grating periods of the source grating and the analyzer grating and in accordance with the position relationships between gratings. Specifically, the amount of displacement $\xi_0$ of the filter $H_S$ with respect to $C(\xi, \eta)$ is determined in accordance with the difference between $1/d_0'$ and $1/d_{IP}$, and the amount of displacement $\xi_2$ of the filter $H_D$ with respect to $C(\xi, \eta)$ is determined in accordance with the difference between $1/d_2$ and $1/d_{IP}$. Thus, the adjustment of the values $d_{IP}$, $d_0'$, and $d_2$ enables control of the influence of the frequency filters described above.

The Talbot interferometer of the related art, which is the Talbot interferometer according to Comparative Example 1, is generally designed to meet $d_0'=d_2=d_{IP}$. Thus, $\xi_0=\xi_2=0$ is established. Here, if a composite filter of $H_S$ and $H_D$ to be applied to the spectrum $C(\xi, \eta)$ of the sample information is represented by $H_C$ and is defined as

[Math. 24]

$$H_C(\xi,\eta)=H_g(\xi-\xi_0,\eta)H_D(\xi-\xi_2,\eta), \qquad (23)$$

Expression (20) can be rewritten as

[Math. 25]

$$C_R(\xi, \eta) = \frac{1}{8}C(\xi, \eta)H_C(\xi, \eta). \qquad (24)$$

While the foregoing description has been made taking as an example the technique of intensity distribution measurement with the movement of the analyzer grating, the information can also be acquired by the movement of the beam splitter grating or the source grating. In addition, such separation of the spectra may be performed using a method other than the phase shift method. For example, separation of the spectra may be performed by generating a moiré pattern having a comparatively short period, applying a Fourier transform to an intensity distribution detected by the X-ray detector, and filtering the spectra in the frequency space. The arithmetic is performed in the sample information acquisition unit.

Next, given that the X-ray emission spot has a two-dimensional Gaussian light emission intensity distribution, $g_S(x_0, y_0)$ can be expressed by

[Math. 26]

$$g_S(x_0, y_0) = e^{-\frac{x_0^2+y_0^2}{2\sigma_S^2}}, \qquad (25)$$

where $\sigma_S$ is a constant that defines the degree of spatial spread of the X-ray emission spot. In this case, $h_S(x, y)$ can be expressed as the following expression by using Expression (9):

[Math. 27]

$$h_S(x, y) \propto e^{-\frac{x^2+y^2}{2\sigma_S'^2}}, \qquad (26)$$

where $\sigma_S'$ is given by

[Math. 28]

$$\sigma_S' = \sigma_S \frac{L_{12}}{L_{01}}. \qquad (27)$$

In this case, $H_S(\xi, \eta)$, which is the Fourier transform of $h_S(x, y)$, can be expressed by the following equation if coefficients are ignored:

[Math. 29]

$$H_S(\xi, \eta) = e^{-\frac{\xi^2+\eta^2}{2\sigma_{SF}^2}}. \qquad (28)$$

Thus, $H_S(\xi, \eta)$ also has a Gaussian shape. In the equation given above, $\sigma_{SF}$ is a constant that defines the width of $H_S(\xi, \eta)$, and is given by

[Math. 30]

$$\sigma_{SF} = \frac{1}{2\pi\sigma_S'} = \frac{1}{2\pi\sigma_S}\frac{L_{01}}{L_{12}}. \qquad (29)$$

Similarly, given that the point spread function specific to the X-ray detector also has a two-dimensional Gaussian shape, $h_D(x, y)$ can be expressed by

[Math. 31]

$$h_D(x, y) \propto e^{-\frac{x^2+y^2}{2\sigma_D^2}}, \qquad (30)$$

where $\sigma_D$ is a constant that defines the width of $h_D(x, y)$. In this case, if coefficients are ignored, $H_D(\xi, \eta)$, which is the Fourier transform of $h_D(x, y)$, is calculated by

[Math. 32]

$$H_D(\xi, \eta) = e^{-\frac{\xi^2+\eta^2}{2\sigma_{DF}^2}}, \qquad (31)$$

where $\sigma_{DF}$ is given by

[Math. 33]

$$\sigma_{DF} = \frac{1}{2\pi\sigma_D}. \qquad (32)$$

In this case, the composite filter $H_C(\xi, \eta)$ to be applied to the spectrum $C(\xi, \eta)$ of sample information, which is defined by Expression (23), can be expressed by

[Math. 34]

$$H_C(\xi, \eta) = H_S(\xi - \xi_0, \eta)H_D(\xi - \xi_2, \eta) \qquad (33)$$
$$= e^{-\frac{(\xi-\xi_0)^2+\eta^2}{2\sigma_{SF}^2}} e^{-\frac{(\xi-\xi_2)^2+\eta^2}{2\sigma_{DF}^2}}$$
$$= e^{-\frac{(\xi_D-\xi_2)^2}{2(\sigma_{SF}^2+\sigma_{DF}^2)}} e^{-\frac{(\xi-\xi_C)^2+\eta^2}{2\sigma_{CF}^2}},$$

where $\xi_C$ and $\sigma_{CF}$ are given by

[Math. 35]

$$\xi_C = \frac{\sigma_{DF}^2 \xi_0 + \sigma_{SF}^2 \xi_2}{\sigma_{SF}^2 + \sigma_{DF}^2} \qquad (34)$$

and

[Math. 36]

$$\sigma_{CF} = \frac{\sigma_{SF}\sigma_{DF}}{\sqrt{\sigma_{SF}^2 + \sigma_{DF}^2}}, \qquad (35)$$

respectively.

As is seen from Expression (33), here, the composite filter $H_C(\xi, \eta)$ to be applied to $C(\xi, \eta)$, which is the spectrum of sample information, has a Gaussian shape, and, as is seen from Expression (35), $\sigma_{CF}$, which represents the filter width, does not depend on $\xi_0$ or $\xi_2$. Thus, it is more preferable to satisfy the condition of $\xi_0 = \xi_2$ in order to transmit a larger amount of components of $C(\xi, \eta)$ by maximizing the integrated value of $|H_C(\xi, \eta)|$. Also, as is seen from Expression (34), $\xi_C = \xi_0 = \xi_2$ is established.

Next, a difference between the Talbot interferometer according to this embodiment and the Talbot interferometer according to Comparative Example 1 will be described using simulation results. The Talbot interferometer according to Comparative Example 1 corresponds to the Talbot interferometer according to this embodiment when the rate of deviation $\alpha_1$ for the grating period is zero. Thus, performance comparison can be made through simulation using formulas similar to those in this embodiment. As used here, the Talbot interferometer according to Comparative Example 1 is an interferometer designed to satisfy $d_0'=d_2=d_{IP}$. As used here, furthermore, the Talbot interferometer according to this embodiment is an interferometer designed to satisfy $d_0'=d_2\neq d_{IP}$. It is also assumed here that $h_S$ and $h_D$ are Gaussian-shaped functions.

Figure 3:
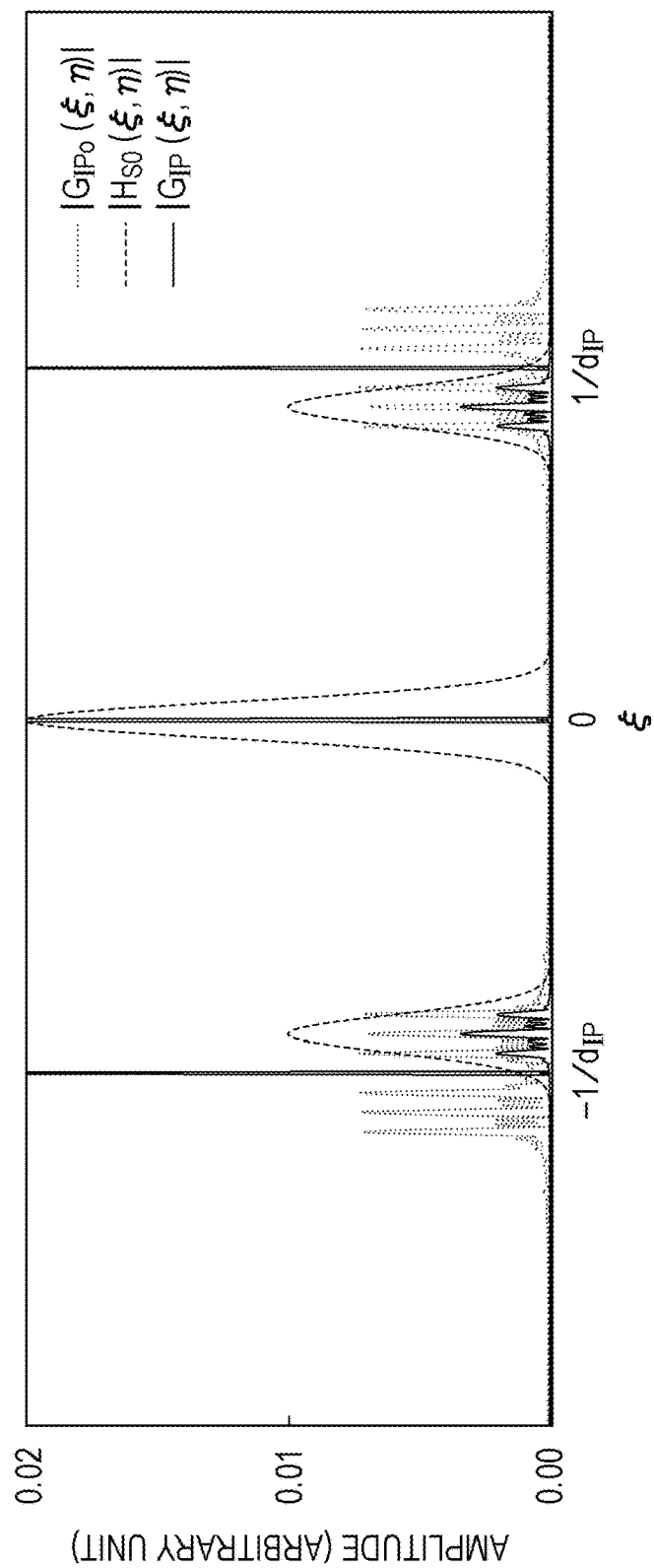
FIG. 3 illustrates an example of spectra of an interference pattern obtained in the first embodiment.

FIG. 3 and FIG. 7 illustrate examples of spectrum shapes obtained as a result of simulation based on the foregoing explanation. In FIG. 3 and FIG. 7, the profiles of the spectra on the $\xi$ axis are illustrated. In FIG. 3 and FIG. 7, $G_{IPo}(\xi, \eta)$ represents a spectrum (spectrum before filtering with $H_{SO}(\xi, \eta)$ is applied) obtained by the Fourier transform of the intensity distribution of an interference pattern formed by X-rays originating from a single point on the source grating. Further, $H_{SO}(\xi, \eta)$ represents a frequency filter that represents the effect of the source grating and the spatial spread of the X-ray emission spot. $G_{IP}(\xi, \eta)$ represents a spectrum obtained by the Fourier transform of the intensity distribution of an interference pattern that is influenced by the source grating and the spatial spread of the X-ray emission spot.

Figures 2, 4A:
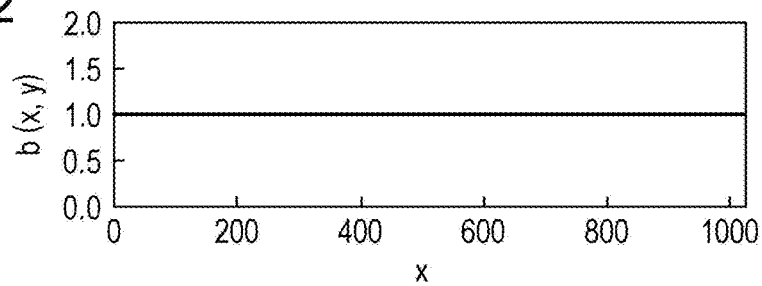
Figures 1, 4B:
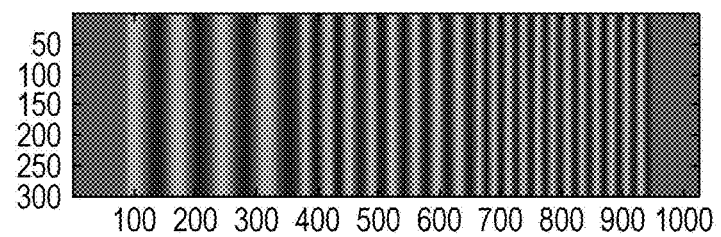
Figures 2, 4B:
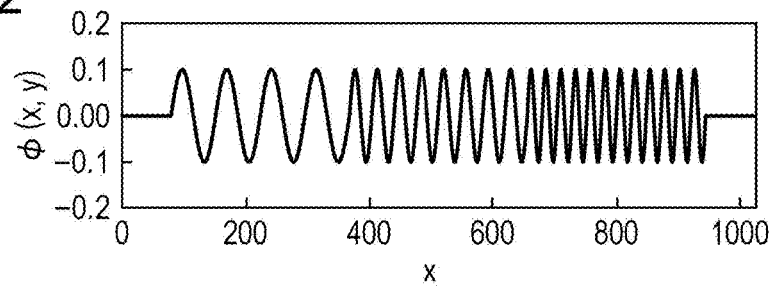

FIG. 4A-1 depicts an image of a set value of $b(x, y)(=|c(x, y)|)$ in this simulation, and FIG. 4B-1 depicts an image of a set value of $\phi(x, y)(=\arg[c(x, y)])$ in this simulation. FIGS. 4A-2 and 4B-2 depict profiles of the images depicted in FIGS. 4A-1 and 4B-1 on the x axis, respectively. As illustrated in FIGS. 4A-1, 4A-2, 4B-1, and 4B-2, here, a distribution having a periodic pattern, in the x direction, with three different periods for individual regions is set as $\phi(x, y)$. In contrast, it is assumed that $b(x, y)=1$. Note that it is assumed that $a(x, y)=1$.

FIG. 7 illustrates spectra for $d_0'=d_{IP}$, that is, for the X-ray Talbot-Lau interferometer of the related art (Comparative Example 1). The illustrated conditions are those of the Talbot-Lau interferometer of the related art illustrated in FIG. 6, and spatial frequency components in an interference pattern which are enhanced by the source grating through superposition of a plurality of interference patterns match the carrier of sample information.

An examination of FIG. 7 reveals that, in Comparative Example 1, $G_{IPo}(\xi, \eta)$, which is the spectrum of the ideal interference fringe intensity distribution, changes to $G_{IP}(\xi, \eta)$ as a result of being filtered with $H_{SO}(\xi, \eta)$. $G_{IPo}(\xi, \eta)$, which is the spectrum of the interference pattern before spectrum deformation, has a significantly high carrier peak, and sidebands which are generated in a nearby frequency domain due to the modulation of the carrier. Here, sample information is mainly included in the sidebands, where a frequency component closer to the carrier corresponds to a lower frequency component in $c(x, y)$ and a frequency component farther from the carrier corresponds to a higher frequency component in $c(x, y)$. In general, $c(x, y)$ contains a phase term. Thus, the upper sideband and the lower sideband are not always completely symmetric. In many cases, the upper sideband and the lower sideband have a shape of comparatively high symmetry. In the Talbot-Lau interferometer according to Comparative Example 1, the carrier ($\xi=\pm 1/d_{IP}$) is enhanced by the effect of the source grating. In other words, when attention is paid to the change in spectrum from $G_{IPo}(\xi, \eta)$ to $G_{IP}(\xi, \eta)$ on the positive side of the $\xi$ axis, the portion of $H_{SO}(\xi, \eta)$ corresponding to the $(½)H_S(\xi-1/d_0', \eta)$ term functions as a bandpass filter, and the center of the Gaussian-shaped portion corresponding to the $(½)H_S(\xi-1/d_0', \eta)$ term matches the carrier frequency. Accordingly, whereas a comparatively large amount of components in the sideband corresponding to the sample information $C(\xi-1/d_0', \eta)$ which are close to the carrier are transmitted, the amount of components transmitted which are far from the carrier significantly decreases. This implies that high-frequency components in the sample information $c(x, y)$ largely attenuate. The frequency enhanced by the source grating refers to a frequency at which a region (the portion corresponding to the $(½)H_S(\xi-1/d_0', \eta)$ term) in $H_{SO}(\xi, \eta)$ which affects the carrier has a local maxima. In other words, the frequency enhanced by the source grating refers to $1/d_0'$. The value $d_0'$ can be calculated once the configuration of the source grating and the beam splitter grating and the geometry of these gratings and the analyzer grating (or the X-ray detector if the analyzer grating is not included) are determined.

Figures 1, 8A:
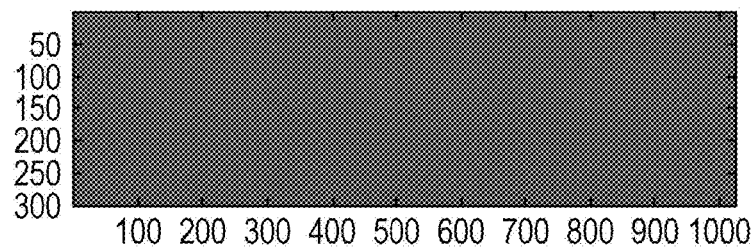
Figures 2, 8A:
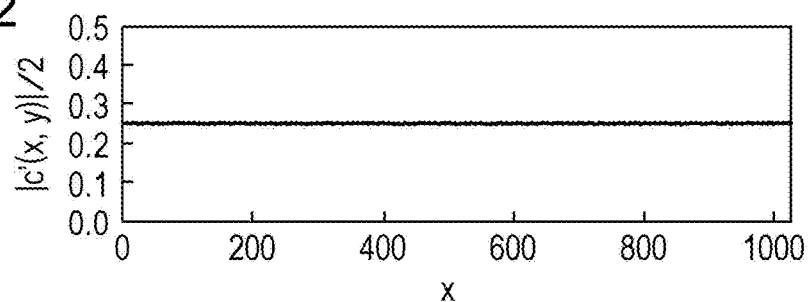
Figures 1, 8B:
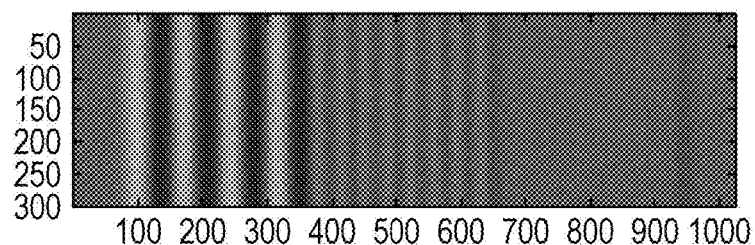
Figures 2, 8B:
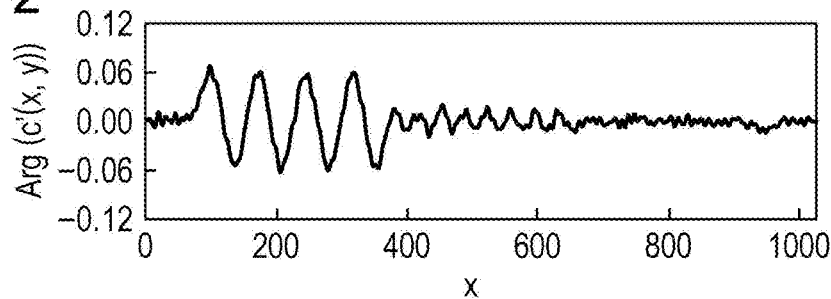

FIGS. 8A-1, 8A-2, 8B-1, and 8B-2 illustrate sample information $c(x, y)$ which has undergone spectrum deformation by the filter $H_{SO}(\xi, \eta)$ (referred to as $c'(x, y)$) and corresponding profiles on the x axis. FIGS. 8A-1 and 8B-1 illustrate images of $|c'(x, y)|/2$ and $\arg[c'(x, y)]$, and FIGS. 8A-2 and 8B-2 illustrate the profiles of the respective images on the x axis. In this simulation, a certain amount of noise is added. As is anticipated from the change in spectrum described above, comparing FIGS. 8A-1, 8A-2, 8B-1, and 8B-2 with FIGS. 4A-1, 4A-2, 4B-1, and 4B-2 shows that high-frequency components apparently attenuate in the image and the signal-to-noise ratio decreases, resulting in a difficulty in detection.

In contrast, FIG. 3 depicts an example of spectrum shapes in the X-ray Talbot interferometer according to this embodiment. In the depicted example, $d_0'$ is slightly larger than $d_{IP}$.

An examination of FIG. 3 reveals that the change in spectrum from $G_{IPo}(\xi, \eta)$ to $G_{IP}(\xi, \eta)$ occurs in the Talbot interferometer according to this embodiment. Since $d_0'$ is slightly larger than $d_{IP}$, spatial frequency components which are enhanced by the source grating through superposition of a plurality of interference patterns are located near the center of the lower sideband generated by the modulation of the carrier by the sample. In other words, when attention is paid to the change in spectrum from $G_{IPo}(\xi, \eta)$ to $G_{IP}(\xi, \eta)$ on the positive side of the $\xi$ axis, the center of the bandpass filter (a local maxima of $(\frac{1}{2})H_S(\xi-1/d_0', \eta)$) does not match the carrier, and is located near the center of the lower sideband within the sidebands generated by modulation by the sample. Here, the bandpass filter is, similarly to FIG. 7, the portion of $H_{S0}(\xi, \eta)$ corresponding to the $(\frac{1}{2})H_S(\xi-1/d_0', \eta)$ term, and has a Gaussian shape. Accordingly, the upper sideband substantially disappears. On the other hand, it is revealed that a large amount of lower sideband components that are far from the carrier remain, compared to FIG. 7. That is, components to be substantially transmitted in the sidebands corresponding to the sample information $C(\xi-1/d_{IP}, \eta)$ are mainly components in one sideband. Thus, compared to the transmission spectrum $G_{IP}(\xi, \eta)$ in the comparative example illustrated in FIG. 7, there is a tendency for a comparatively large amount of high-frequency components in $c(x, y)$ to remain. The spatial frequency components to be enhanced may be located near the center of the upper sideband generated by the modulation of the carrier by the sample. Instead of components near the center of a sideband, a component within the sideband may be enhanced. To this end, it may be sufficient that the local maxima of the portion of $H_{S0}(\xi, \eta)$ corresponding to the $(\frac{1}{2})H_S(\xi-1/d_0', \eta)$ term matches a component within a sideband generated by modulation by the sample.

Figures 1, 5A:
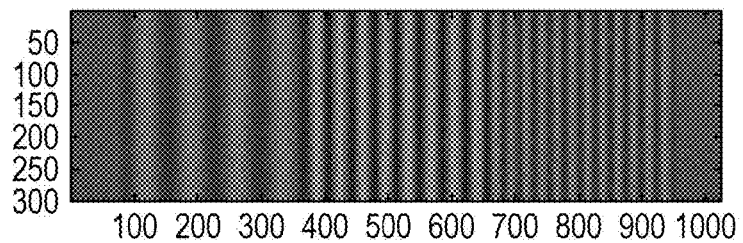
Figures 2, 5A:
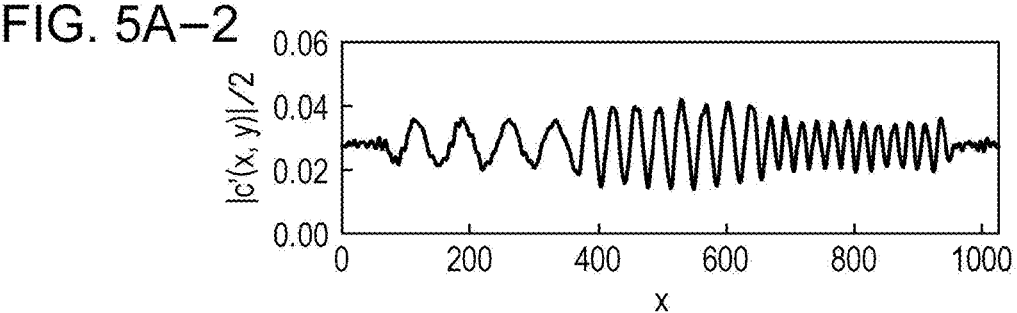
Figures 1, 5B:
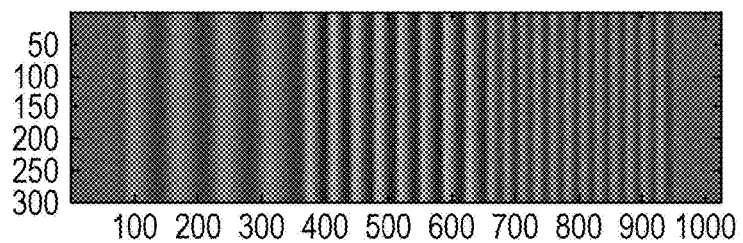
Figures 2, 5B:
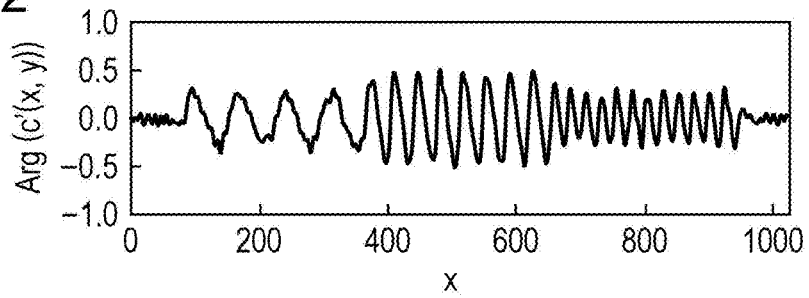

FIGS. 5A-1, 5A-2, 5B-1, and 5B-2 illustrate $c'(x, y)$, which is sample information $c(x, y)$ that has undergone spectrum deformation by the filter $H_{S0}(\xi, \eta)$, and corresponding profiles on the x axis. FIGS. 5A-1 and 5B-1 illustrate images of $|c'(x, y)|/2$ and $\arg[c'(x, y)]$, and FIGS. 5A-2 and 5B-2 illustrate the profiles of the respective images on the x axis. Also in this simulation, an equivalent amount of noise to that in Comparative Example 1 is added. As is anticipated from the change in spectrum described above, comparing FIGS. 5A-1, 5A-2, 5B-1, and 5B-2 with FIGS. 8A-1, 8A-2, 8B-1, and 8B-2 and FIGS. 4A-1, 4A-2, 4B-1, and 4B-2 shows that a large amount of high-frequency components in the image remain, compared to Comparative Example 1, and detection performance is improved. In FIGS. 5A-1 and 5A-2, a sample image that is not shown in FIGS. 4A-1 and 4A-2 appears because, due to the effect of asymmetry of a frequency filter with respect to the carrier, information on $\phi(x, y)$ also appears on the absolute-value side of $c'(x, y)$. That is, the correlation between $|c'(x, y)|$ and $b(x, y)$ and the correlation between $\arg(c'(x, y))$ and $\phi(x, y)$ become weak. Likewise, although not shown in this simulation results, this embodiment has a secondary effect that information on $b(x, y)$ also appears on the argument side of $c'(x, y)$.

Next, a description will be given of the result of simulation of all the steps of calculating a restored value $C_R(\xi, \eta)$ of sample information by using the phase shift method as described above, assuming the presence of the analyzer grating.

Figure 9A:
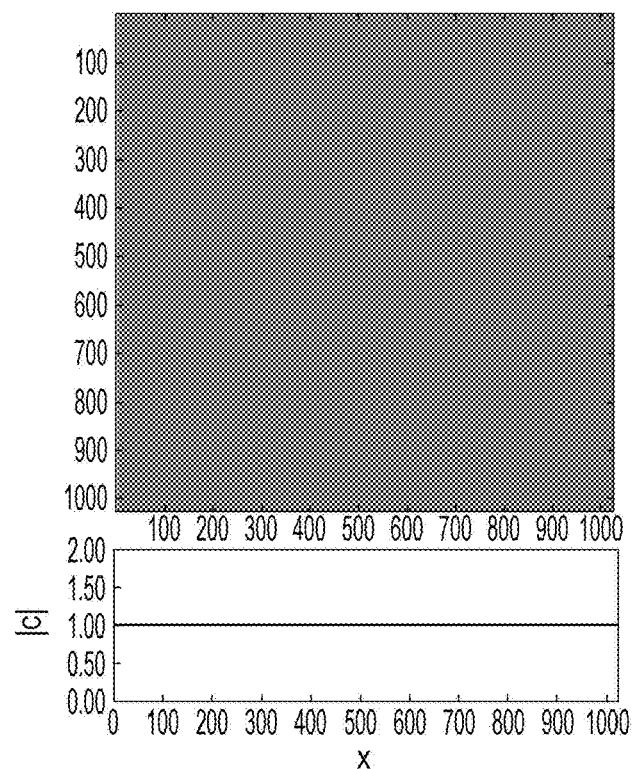
FIGS. 9A and 9B illustrate an example of pieces of sample information in the first embodiment.
Figure 9B:
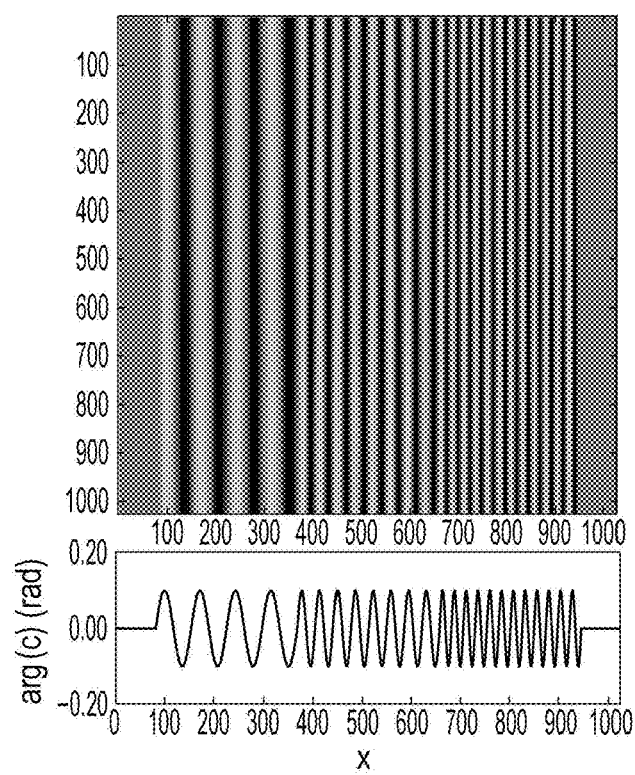

FIGS. 9A and 9B depict images of set values of $|c(x, y)|$ and $\arg[c(x, y)]$ in this simulation, respectively, and corresponding profiles on the x axis. Note that it is assumed that $a(x, y)=1$.

Figure 13A:
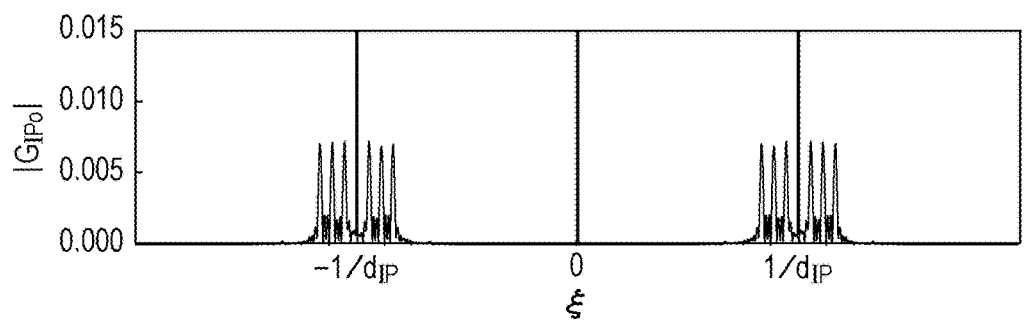
FIGS. 13A to 13C illustrate an example of spectra of an interference pattern obtained in Comparative Example 1.
Figure 13B:
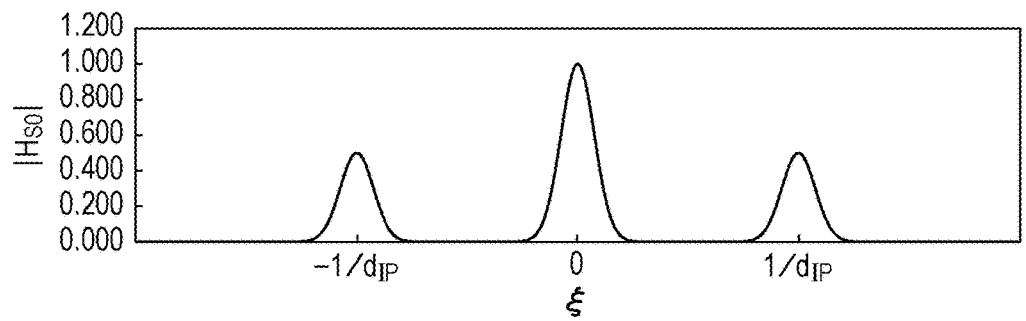
Figure 13C:
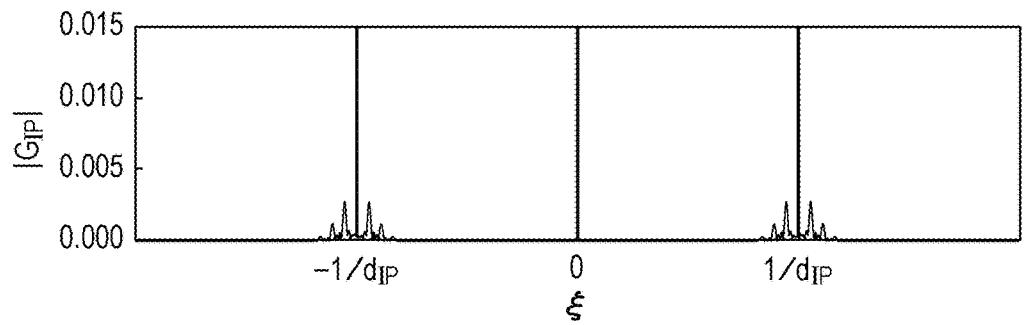

FIGS. 13A, 13B, and 13C illustrate the profiles of $|G_{IPo}(\xi, \eta)|$, $|H_{S0}(\xi, \eta)|$, and $|G_{IP}(\xi, \eta)|$ on the $\xi$ axis in Comparative Example 1, respectively. Detailed conditions are different from those in Comparative Example 1 described above. Similarly to FIG. 7, it is revealed that, due to the effect of $|H_{S0}(\xi, \eta)|$, $|G_{IP}(\xi, \eta)|$ exhibits the enhanced carrier of $|G_{IPo}(\xi, \eta)|$ and the amount of frequency components transmitted which are farther from the carrier decreases.

Figure 14A:
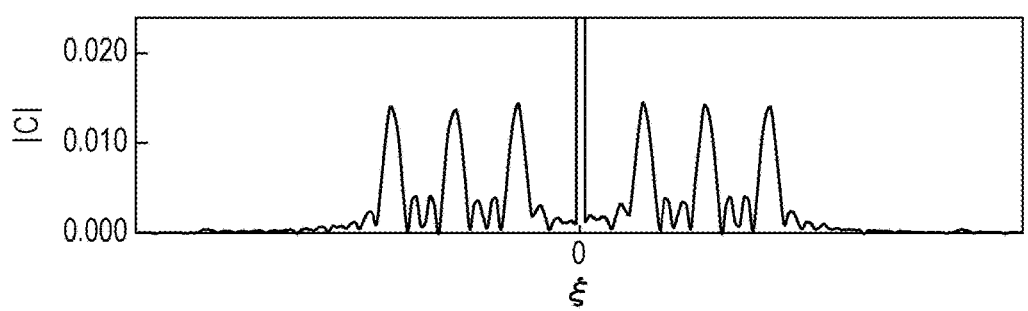
FIGS. 14A to 14C illustrate an example of spectra of sample information restored in Comparative Example 1.
Figure 14B:
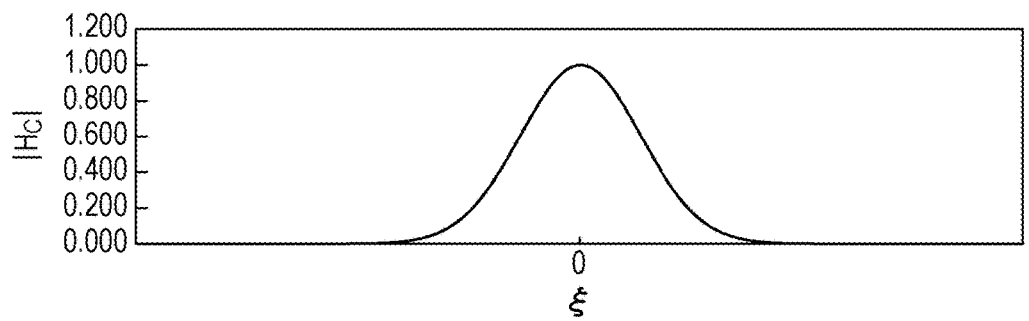
Figure 14C:
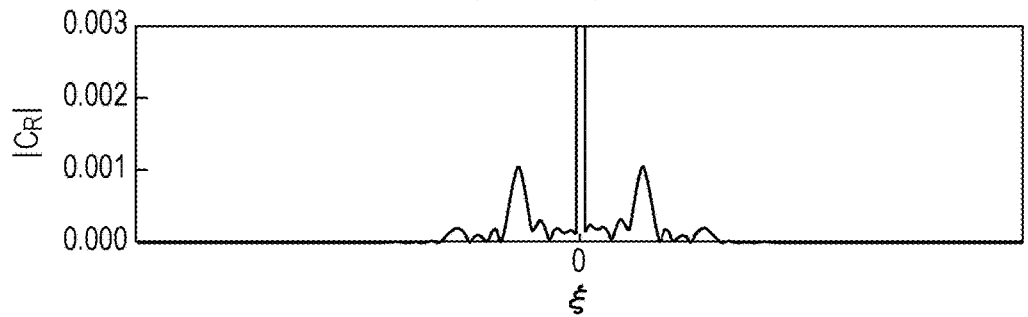
Figure 15A:
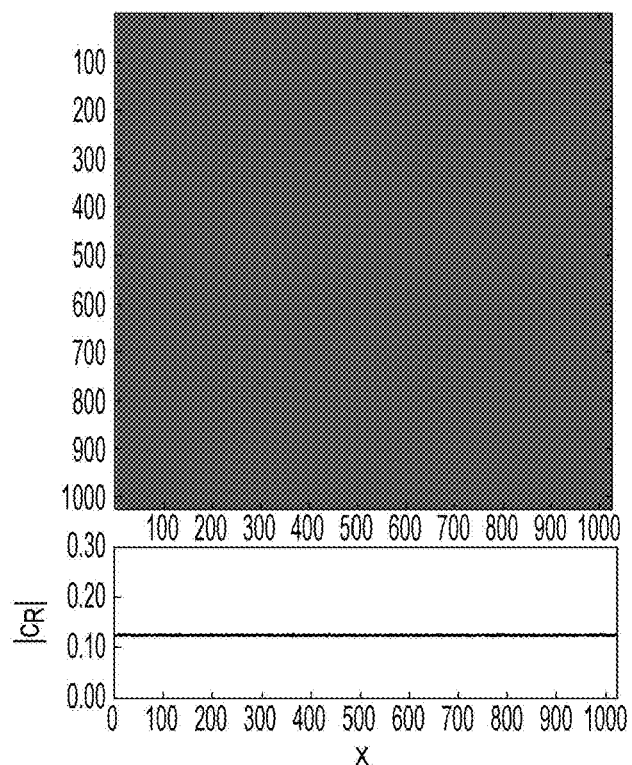
FIGS. 15A and 15B illustrate an example of sample information restored in Comparative Example 1.
Figure 15B:
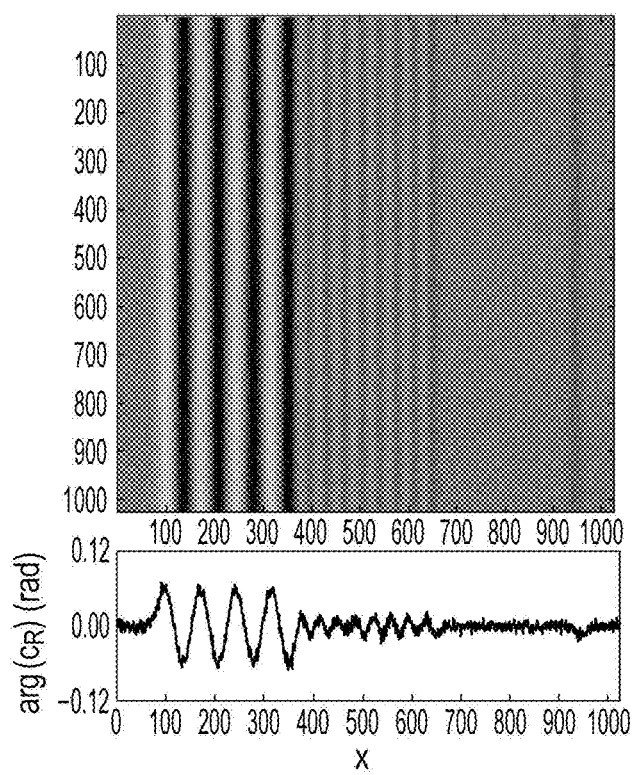

FIGS. 14A, 14B, and 14C depict the results of simulation of all the steps of calculating a restored value $C_R(\xi, \eta)$ of sample information by using the phase shift method, assuming the presence of the analyzer grating. It is assumed here that the analyzer grating has a pitch $d_2$ that matches the carrier. In FIGS. 14A and 14C, lower frequency components of the sample information are closer to the origin, and higher frequency components of the sample information are farther from the origin. FIGS. 14A, 14B, and 14C depict the profiles of $|C(\xi, \eta)|$, $|H_C(\xi, \eta)|$, and $|C_R(\xi, \eta)|$ on the $\xi$ axis, respectively. Since $H_C(\xi, \eta)$ is a composite of $H_S(\xi-\xi_0, \eta)$ and $H_D(\xi-\xi_2, \eta)$, $H_C(\xi, \eta)$ is a filter having a smaller width and a smaller frequency band allowed for transmission than $H_S$ alone. As can be understood from FIGS. 14A, 14B, and 14C, in the Talbot interferometer of the related art, the frequency filter $H_C(\xi, \eta)$ has a local maxima at the origin of the frequency coordinate system, and the profile on the $\xi$ axis has a symmetry about the origin (two-dimensionally, has a point symmetry about the origin). Accordingly, components in a region farther from the origin in $C(\xi, \eta)$ are more largely lost during transmission. In other words, high-frequency components in $c(x, y)$ are largely lost. This can be observed in FIGS. 15A and 15B, which illustrate $c_R(x, y)$, which corresponds to $C_R(\xi, \eta)$.

Figure 10A:
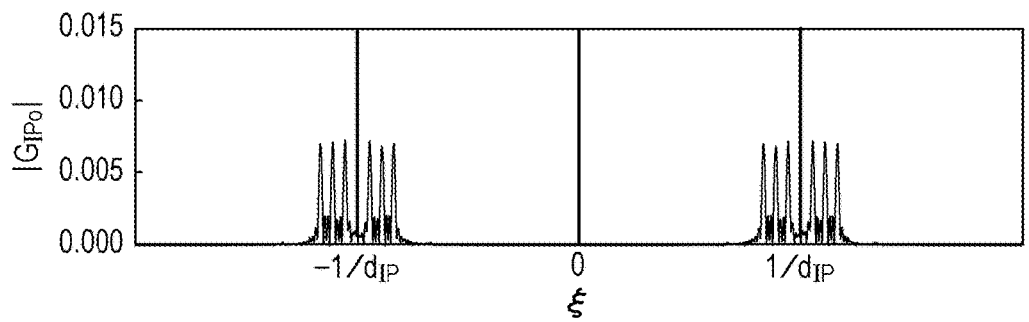
FIGS. 10A to 10C illustrate an example of spectra of an interference pattern obtained in the first embodiment.
Figure 10B:
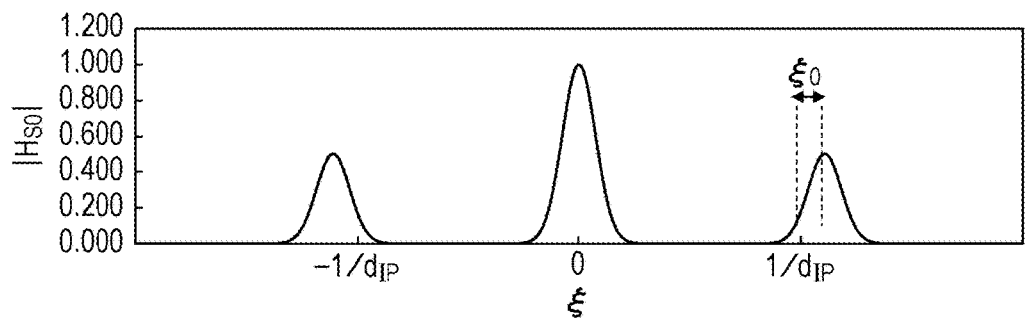
Figure 10C:
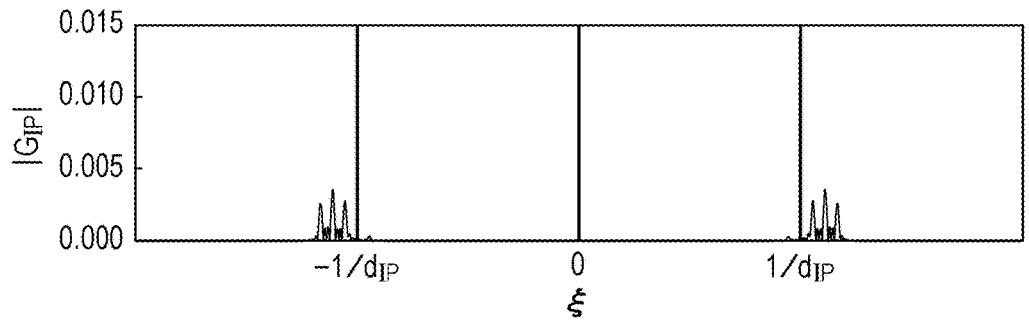

FIGS. 10A, 10B, and 10C illustrate separate portions of the profiles of $|G_{IPo}(\xi, \eta)|$, $|H_{S0}(\xi, \eta)|$, and $|G_{IP}(\xi, \eta)|$ on the $\xi$ axis according to this embodiment. Unlike the example described above, $d_0'$ is assumed to be slightly smaller than $d_{IP}$. Thus, components near the center of the upper sideband are enhanced.

Figure 11A:
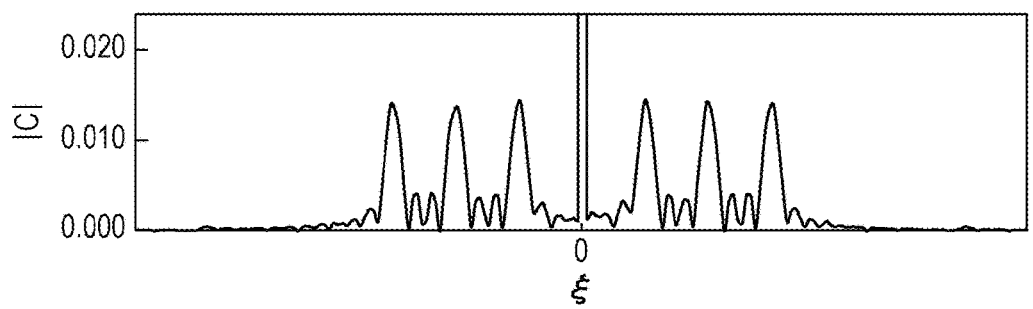
FIGS. 11A to 11C illustrate an example of spectra of sample information restored in the first embodiment.
Figure 11B:
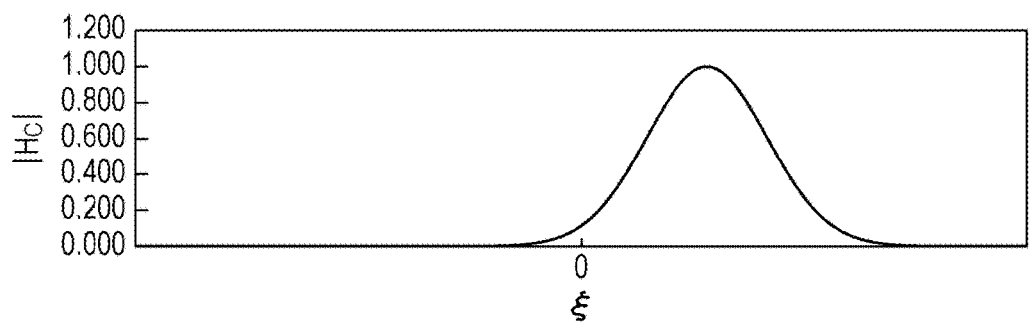
Figure 11C:
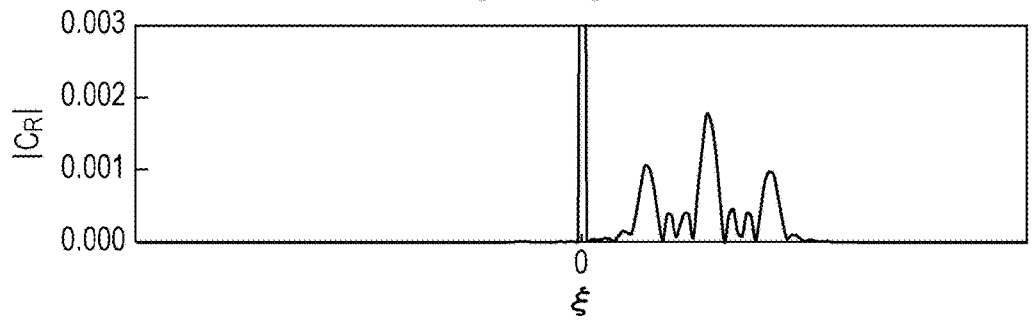
Figure 12A:
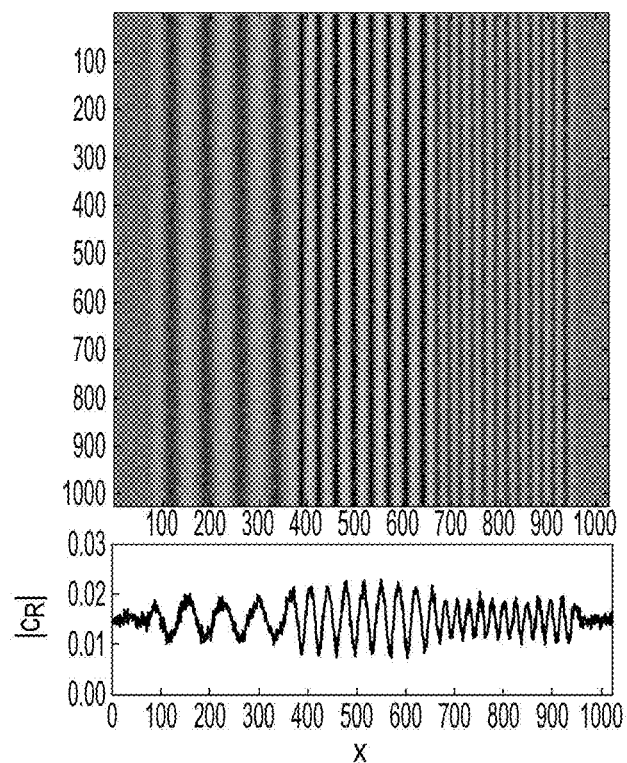
FIGS. 12A and 12B illustrate an example of sample information restored in the first embodiment.
Figure 12B:
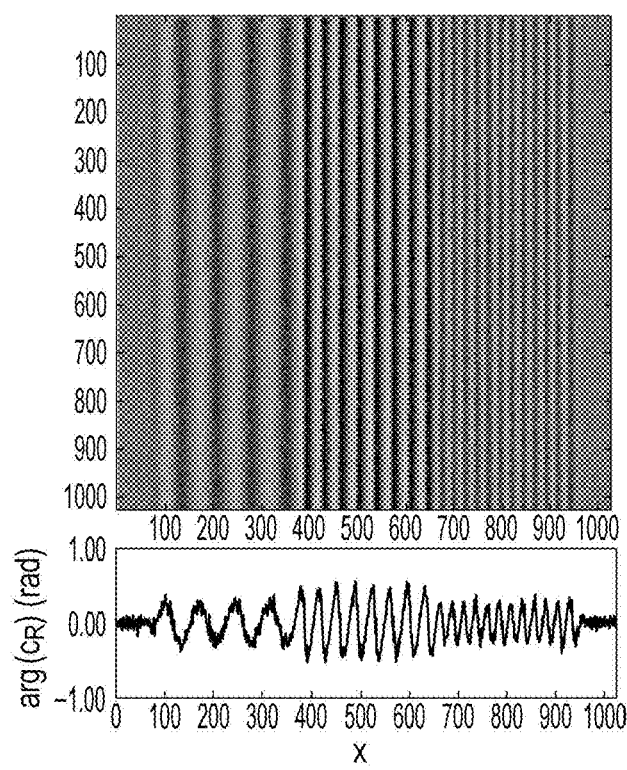

FIGS. 11A, 11B, and 11C illustrate the results of simulation of all the steps of calculating a restored value $C_R(\xi, \eta)$ of sample information with the use of the analyzer grating by using the phase shift method. It is assumed that analyzer grating has a pitch $d_2$ that matches $d_0'$. FIGS. 11A, 11B, and 11C depict the profiles of $|C(\xi, \eta)|$, $|H_C(\xi, \eta)|$, and $|C_R(\xi, \eta)|$ on the $\xi$ axis, respectively. As can be understood from FIGS. 11A, 11B, and 11C, in the Talbot interferometer according to this embodiment, the frequency filter $H_C(\xi, \eta)$ has a local maxima at a position far from the origin of the frequency coordinate system. Accordingly, here, only the components in the region of $\xi>0$ in $C(\xi, \eta)$ are substantially transmitted. Comparing the result with the shape of $|C_R(\xi, \eta)|$ in Comparative Example 1 illustrated in FIG. 14C shows that a larger amount of components in a region farther from the origin in $C(\xi, \eta)$ are transmitted. In other words, a larger amount of high-frequency components in $c(x, y)$ remain. This can be observed in FIGS. 12A and 12B, which illustrate $c_R(x, y)$, which corresponds to $C_R(\xi, \eta)$.

Next, consideration will be given to a preferred range of the values $d_0$ and $d_2$ according to this embodiment.

First, consideration will be given to the stage in which $G_{IPo}(\xi, \eta)$, which is the spectrum of the ideal interference fringe intensity distribution, changes to $G_{IP}(\xi, \eta)$ as a result of being filtered with $H_{S0}(\xi, \eta)$. In this stage, $\xi_0$, which is the frequency difference between the center of the portion of $H_{S0}(\xi, \eta)$ corresponding to the $(\frac{1}{2})H_S(\xi-1/d_0', \eta)$ term and the carrier, can be expressed by

[Math. 37]

$$\xi_0 = \frac{1}{d_0'} - \frac{1}{d_{IP}} = -\frac{1}{d_{IP}} \frac{\alpha_1}{1+\alpha_1} \approx -\frac{\alpha_1}{d_{IP}}, \quad (36)$$

when $n_1=1$ (where $|\alpha_1|\ll 1$). Further, $\sigma_{SF}$ representing the width of $H_S$ having a Gaussian shape is represented by Expression (29). On the other hand, $C(\xi-1/d_{IP}, \eta)$, which is the spectrum of sample information, is centered at the carrier, and is two-dimensionally distributed around the carrier. As described above, $\phi(x, y)$ reflects the distribution obtained by differentiation of the phase distribution of X-rays that have propagated through the sample in the direction of the carrier. Accordingly, the component of $C(\xi-1/d_{IP}, \eta)$ distinctly appears particularly in the $\xi$-axis direction that is the direction of the carrier. It is thus preferable that the filter $H_S$ be shifted along the $\xi$ axis ($\xi_0 \neq 0$ be set). Making $|\xi_0|$ large enables the transmission of a large amount of higher frequency components in $c(x, y)$, and also causes a drawback in that the absence of low-frequency components will result in an unnatural image. In order to achieve the effect of increasing the amount of transmission of high-frequency components while preventing the absence of low-frequency components, it may be sufficient to select $\xi_0$ so as to satisfy

[Math. 38]

$$0.5\sigma_{SF} < |\xi_0| < 3.0\sigma_{SF}. \quad (37)$$

Letting the full width at half maximum of $g_S(x_0, y_0)$ be $w_S$, the relationship of $w_S = 2\sigma_S(2 \ln 2)^{0.5}$ is established when $g_S(x_0, y_0)$ has a Gaussian shape. Thus, Expression (37) can be rewritten as

[Math. 39]

$$0.5\frac{\sqrt{2\ln 2}}{\pi w_S}\frac{L_{01}}{L_{12}} < |\xi_0| < 3.0\frac{\sqrt{2\ln 2}}{\pi w_S}\frac{L_{01}}{L_{12}}. \quad (38)$$

Calculating the coefficient portions and rewriting Expression (38) with $\alpha_1$ yields

[Math. 40]

$$0.2\frac{d_{IP}}{w_S}\frac{L_{01}}{L_{12}} < |\alpha_1| < 1.1\frac{d_{IP}}{w_S}\frac{L_{01}}{L_{12}}. \quad (39)$$

Expression (39) is an expression that gives a preferred range of the rate of deviation $\alpha_1$ for determining the value $d_0$ in this embodiment when taking into account only the width of the light emission intensity distribution ($g_S(x_0, y_0)$) of the X-ray emission spot. While the description is based on the assumption that the light emission intensity distribution $g_S(x_0, y_0)$ of the X-ray emission spot has a Gaussian shape, the light emission intensity distribution $g_S(x_0, y_0)$ may have any other general shape such as the shape of a rectangular function. In this case, although the complexity in the shape of $H_S$ increases, a preferred range of the value $\alpha_1$ matches the range given by Expression (39).

Next, consideration will be given to a preferred range of the value $d_0$ when considering all the steps of calculating a restored value $C_R(\xi, \eta)$ of sample information with the use of the analyzer grating by using the phase shift method.

It may be possible to set $d_2 = d_{IP} \neq d_0'$, for example, when the point spread function for the X-ray detector is sufficiently smaller than the point spread function for the X-ray emission spot. In general, however, as described above, it is preferable that $d_2 = d_0'$ be set. Further, the width $\sigma_{CF}$ of the composite frequency filter $H_C$ when considering all the steps of measurement by using the phase shift method is given by Expression (35), as described above. In this case, a preferred range of $\xi_0 (= \xi_2 = \xi_C)$ can be expressed by the following expression on the basis of a similar way of thinking to that of Expression (37),

[Math. 41]

$$0.5\sigma_{CF} < |\xi_0| < 3.0\sigma_{CF}. \quad (40)$$

Letting the full width at half maximum of $h_D(x, y)$, which is the point spread function specific to the detector, be $w_D$, the relationship of $w_D = 2\sigma_D(2 \ln 2)^{0.5}$ is established when $h_D(x, y)$ has a Gaussian shape. Thus, Expression (40) can be rewritten as

[Math. 42]

$$0.5\frac{\sqrt{2\ln 2}}{\pi\sqrt{\left(w_S\frac{L_{12}}{L_{01}}\right)^2 + w_D^2}} < |\xi_0| < 3.0\frac{\sqrt{2\ln 2}}{\pi\sqrt{\left(w_S\frac{L_{12}}{L_{01}}\right)^2 + w_D^2}}. \quad (41)$$

Calculating the coefficient portions and rewriting Expression (41) with $\alpha_1$ yields

[Math. 43]

$$0.2\frac{d_{IP}}{\sqrt{\left(w_S\frac{L_{12}}{L_{01}}\right)^2 + w_D^2}} < |\alpha_1| < 1.1\frac{d_{IP}}{\sqrt{\left(w_S\frac{L_{12}}{L_{01}}\right)^2 + w_D^2}}. \quad (42)$$

Expression (42) is an expression that gives a preferred range of the rate of deviation $\alpha_1$ for determining the value $d_0$ when taking into account the light emission intensity distribution of the X-ray emission spot and the point spread function of the detector.

Letting the grating period of the beam splitter grating be $d_1$, the relationship between $d_{IP}$ and $d_1$ can be generally expressed by

[Math. 44]

$$d_{IP} = \frac{d_1}{m}\frac{L_{01} + L_{12}}{L_{01}}, \quad (43)$$

where m is a positive integer. The preferred value of m is determined in accordance with the relationship between the pattern of the beam splitter grating and the interference pattern, and, in general, it is preferable to set m=1 or 2. A typical example in a case where it is preferable to set m=1 is the use of the so-called π/2-modulation phase grating as the beam splitter grating. A typical example in a case where it is preferable to set m=2 is the use of the so-called π-modulation phase grating as the beam splitter grating. Also when the harmonic components in the interference pattern are used as the carrier, m takes a value other than 1. Using Expression (43), Expression (39) and Expression (42) can be rewritten with $d_1$ as

[Math. 45]

$$0.2 \frac{d_1}{m w_S} \frac{L_{01} + L_{12}}{L_{12}} < |\alpha_1| < 1.1 \frac{d_1}{m w_S} \frac{L_{01} + L_{12}}{L_{12}} \quad (44)$$

and

[Math. 46]

$$0.2 \frac{d_1 (L_{01} + L_{12})}{m \sqrt{(w_S L_{12})^2 + (w_D L_{01})^2}} < |\alpha_1| < 1.1 \frac{d_1 (L_{01} + L_{12})}{m \sqrt{(w_S L_{12})^2 + (w_D L_{01})^2}}, \quad (45)$$

respectively. Expression (44) and Expression (45) are expressions that give a preferred range of the value $\alpha_1$ when taking into account the point spread function of the detector and when not taking into account the point spread function of the detector, respectively. In addition, in this case, the value $d_0$ can be rewritten with $d_1$ as

[Math. 47]

$$d_0 = \frac{n_1 d_1}{m} \frac{L_{01} + L_{12}}{L_{12}} (1 + \alpha_1). \quad (46)$$

As described above, the integrated value of $|H_C|$ is maximized when $\xi_0 = \xi_2$. Thus, $d_2$ is preferably a value expressed, using $\alpha_1$, which is the same as that defined as the rate of deviation for $d_0$, as

[Math. 48]

$$d_2 = n_2 d_{IP}(1 + \alpha_1), \quad (47)$$

where $n_2$ is a positive integer, and, as described above, preferably, $n_2 = 1$ in terms of transmittance. This expression can be written, using Expression (43), as

[Math. 49]

$$d_2 = \frac{n_2 d_1}{m} \frac{L_{01} + L_{12}}{L_{01}} (1 + \alpha_1). \quad (48)$$

As described above, if the X-ray detector has a sufficiently high spatial resolution, the analyzer grating is not essential, and the intensity distribution $g_{IP}(x, y)$ of the interference pattern may be directly detected. In this case, the point spread function for the X-ray detector is considered to be sufficiently smaller than the point spread function for the X-ray source, and only the point spread function for the X-ray source is thus taken into account. Thus, it may be sufficient that $\xi_0$ is determined so as to fall within the range in Expression (37), and the value $\alpha_1$ is determined so as to fall within the range in Expression (44). For measurement using the analyzer grating, on the other hand, it is more preferable that the value $\alpha_1$ be determined using Expression (45) that shows a more accurate preferred range. In particular, when $w_D$, which represents the width of $h_D$, has a value at least as large as the value given by $w_S \times (L_{12}/L_{01})$, which represents the width of $h_S$, the difference between the ranges of the value $\alpha_1$ given by Expression (45) and Expression (44) is large. Thus, it is particularly preferable that Expression (45) be used. Note that if the value $\alpha_1$ does not even satisfy Expression (45) but satisfies Expression (44), it is possible to transmit higher components than ($\alpha_1 = 0$) in the related art, enabling an improvement in spatial resolution.

Further, the method for measuring the light emission intensity distribution of the X-ray emission spot and the point spread function of the detector are well known, and $w_S$, which is the full width at half maximum of the light emission intensity distribution of the X-ray emission spot, and $w_D$, which is the full width at half maximum of the point spread function of the detector, can be easily measured. Examples of the simple method include measurement based on a result of imaging with a pinhole placed at a predetermined position that is in an X-ray path in the imaging system. Accordingly, it is easy to verify whether or not the interferometer satisfies the conditions in Expressions (44) to (48).

It may be likely that setting the value $|\alpha_1|$ to be comparatively large will result in a reduction in the quality of an image when $c_R(x, y)$ is displayed as an image because of a significantly small value of the carrier component. To address this issue, the following process may be performed: The component corresponding to the carrier is numerically restored, and the restored value is added to the calculated function $c_R(x, y)$. For imaging of $c_R(x, y)$, which is a complex-valued distribution function, imaging by mapping the real part and the imaginary part may be performed, for example, instead of, as described above by way of example, imaging by mapping the absolute value and the argument. The component corresponding to the carrier may be restored by, for example, constant multiplication of only the component of a carrier with peak frequency in $C_R(\xi, \eta)$.

Furthermore, among the sidebands in $G_{IP_o}(\xi, \eta)$, components in the upper sideband may be transmitted by setting $\alpha_1 < 0$, or components in the lower sideband may be transmitted by setting $\alpha_1 > 0$. As described above, information on the sample appears not only as amplitude modulation of the interference pattern but also as phase modulation. Thus, in general, the amplitude spectrum of the upper sideband and the amplitude spectrum of the lower sideband are not completely symmetric. Further, depending on the type of the sample, selection of the upper or lower sideband for transmission might cause large differences in the visibility of the structure of the sample or in detection performance. Accordingly, in view of the above-described relationships, it is more preferable to set the value $\alpha_1$ so that a region to be transmitted (enhanced) within a sideband predicted in advance can be located near the local maxima of a region of the frequency filter $H_S$ that is to be applied to the carrier. Another configuration which allows a user to set the size of the sample that the user particularly wishes to observe (enhance) may be used. In this case, it may be sufficient to provide a setting unit that allows the user to set a size, a computation device, and a unit that places a source grating determined from among a plurality of included source gratings in an optical path. The computation device includes a unit that determines a frequency to be enhanced in accordance with the set size, a unit that determines the value $\alpha_1$ in accordance with the distance ($\xi_0$) between the determined frequency and the carrier, and a unit that determines a source grating to be used in accordance with the determined value $\alpha_1$. The setting unit may include, for example, a dial or button to enter a value, a display unit to display a set value, and so forth. The unit that places the determined source grating in the optical path may be a moving unit (which may be an actuator, a gear, or the like) that moves the source grating in response to an instruction from the computation device. Instead of a source grating to be used being changed over among a plurality of source gratings, a source grating whose pitch can be changed (for example, the source grating described in Japanese Laid-Open No. 2011-153869) may be used.

Further, in order to effectively improve spatial resolution according to an embodiment of the present invention, preferably, a measurement technique that is based on obtaining a moiré image a plurality of times, such as a phase shift method, is used particularly when the spatial resolution of the detector is not sufficiently high, to make maximum use of the detection spatial frequency bandwidth of the detector.

As described above in this embodiment, furthermore, when the condition of $\xi_2 \neq 0$ is satisfied by setting $d_2 \neq d_{IP}$, there is a displacement of $\xi_2$ between the center of the spectrum $G_M(\xi, \eta, k)$ of the X-ray intensity distribution acquired by the detector and the center of the spectrum C of sample information. The displacement between the centers of the spectra may be corrected by frequency shifting in a computer in a stage such as after the calculation of $C_R$, or may be corrected by performing division operation by reference data obtained as a result of measurement when no sample is placed. In this case, since the center of $C_R$ is shifted in the frequency coordinate system, the entire $C_R$ will generally lie beyond a detection spatial frequency band inherent in the detector. To address this potential situation, preferably, a frequency band wider than the inherent detection spatial frequency band of the detector is prepared in the computer, and $C_R$ is contained within the frequency band so that the center of $C_R$ matches the origin of the frequency coordinate system. In other words, preferably, the data interval (the pixel pitch of an image) of image data corresponding to $c_R(x, y)$ that the interferometer system displays or records is set to be smaller than the inherent pixel pitch (a sampling interval) of the detector.

Second Embodiment

A description will be given of a Talbot interferometer according to this embodiment that does not include a source grating, in which a component in a sideband caused by modulation by a sample is enhanced by an analyzer grating. In an X-ray Talbot interferometer of the related art (including an X-ray Talbot-Lau interferometer), the analyzer grating makes a band, which is centered at the carrier of the interference pattern formed on the analyzer grating, detectable by the X-ray detector by frequency shifting. In this embodiment, frequency shifting is performed by the analyzer grating so that the center of the band to be detectable by the X-ray detector is shifted from the carrier, thereby achieving an improvement in spatial resolution. The details will be described hereinafter.

In this embodiment, no source grating is included. Thus, unlike the first embodiment, a plurality of interference patterns are not superimposed on one another (i.e., the Talbot interferometer according to this embodiment is not a Talbot-Lau interferometer), and the analyzer grating has a pitch $d_2$ that is different from the period of the interference pattern formed on the analyzer grating. Other configuration is similar to that in the first embodiment, and a redundant portion is not described herein.

Figure 19:
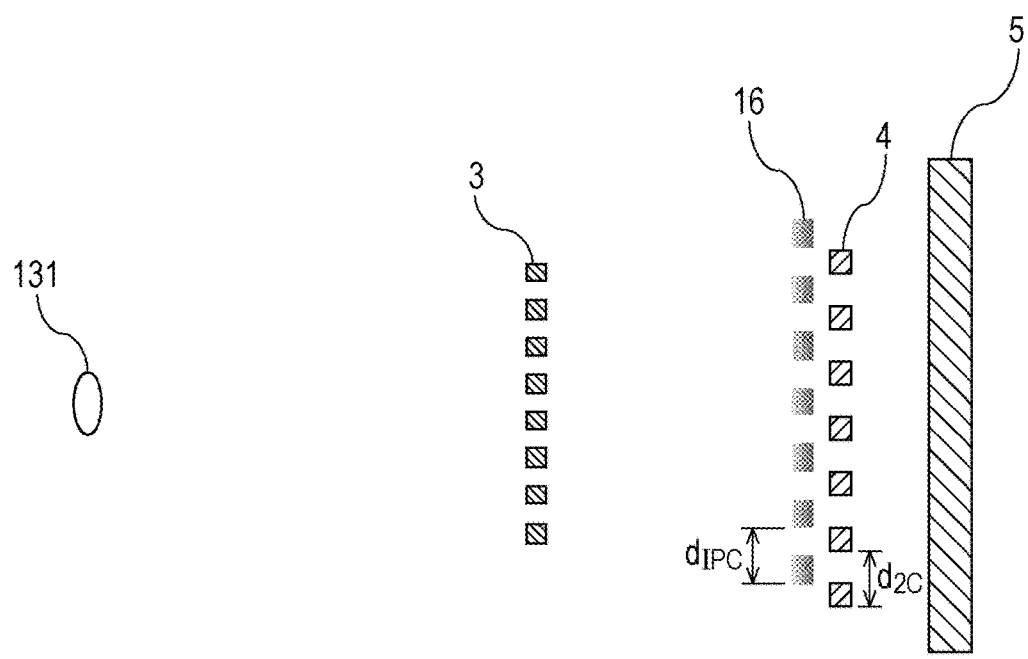
FIG. 19 is a schematic diagram of an X-ray Talbot interferometer according to Comparative Example 2.

FIG. 19 is a schematic diagram of an X-ray Talbot interferometer 1300 according to Comparative Example 2. The X-ray Talbot interferometer 1300 includes an X-ray source 131, a beam splitter grating 3, an analyzer grating 4, and an X-ray detector 5.

In the Talbot interferometer 1300 of the related art, as described above, the analyzer grating 4 is placed at the position where an interference pattern 16 occurs so that moiré fringes are generated on the intensity distribution of the X-rays that have passed through the analyzer grating 4 to assist the X-ray detector 5 in performing intensity distribution measurement. The analyzer grating 4 is generally designed to have a grating period $d_{2C}$ that is equal to a period $d_{IPC}$ of the interference pattern 16 which is obtained when no sample or the like is placed in X-ray paths from the X-ray source 131 to the analyzer grating 4. If the periodic direction of the interference pattern 16 coincides with the periodic direction of the analyzer grating 4, an infinite moiré period is obtained. Thus, if the X-ray detector 5 is a detector incapable of resolving the period of the interference pattern itself, no fringe pattern is detected. Further, if the periodic directions of the interference pattern 16 and the analyzer grating 4 are slightly displaced with respect to each other on a surface of the analyzer grating 4, moiré fringes having a periodic direction substantially perpendicular to the periodic direction of the analyzer grating 4 occur. In general, a Talbot interferometer adjusts the moiré period by adjusting the relative rotation angles of the interference pattern and the analyzer grating.

Figure 16:
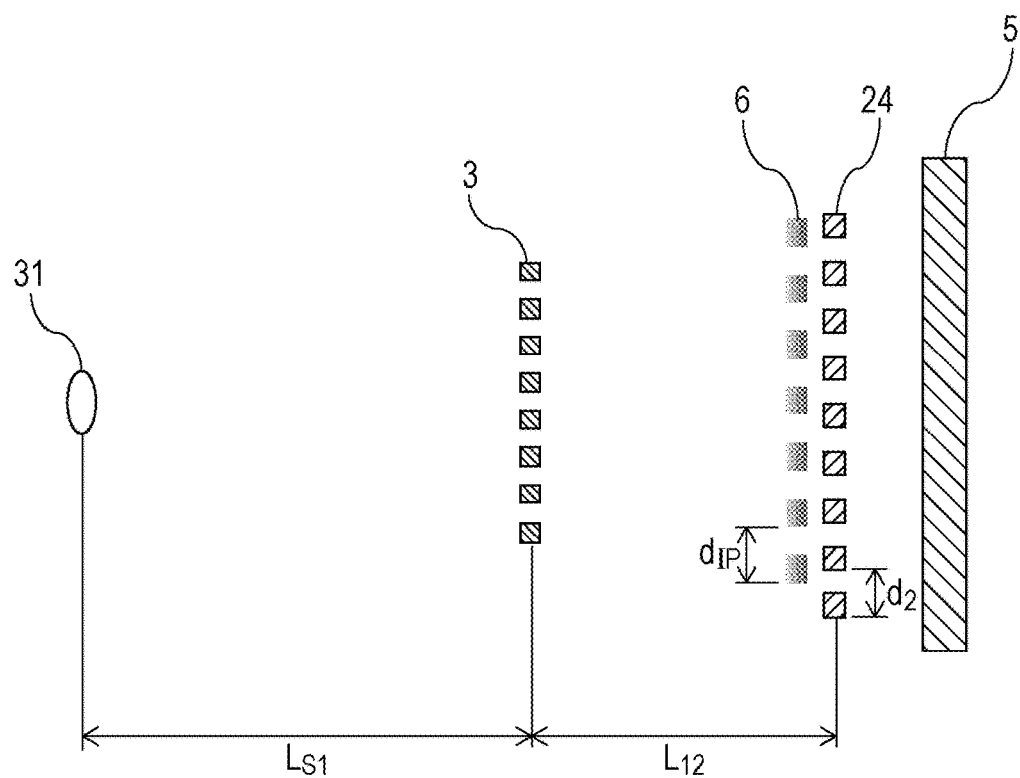
FIG. 16 is a schematic diagram of an X-ray Talbot interferometer according to the second embodiment.

In contrast, as illustrated in FIG. 16, an X-ray Talbot interferometer 300 according to this embodiment is designed so that an analyzer grating 24 has a grating period $d_2$ that is not equal to a period $d_{IP}$ of an interference pattern 6 which is obtained when no sample or the like is placed in X-ray paths from an X-ray source 31 to the analyzer grating 24. In this case, moiré fringes are formed in the detection region. Unlike the moiré pattern caused by the relative rotations of the interference pattern 6 and the analyzer grating 24, which has been described above, the periodic direction of the moiré fringes is the same as the periodic direction of the analyzer grating 24.

This embodiment will be described in more detail hereinafter.

The X-ray Talbot interferometer 300 according to this embodiment includes a beam splitter grating 3 that forms the interference pattern 6, the analyzer grating 24 that blocks some of the X-rays which form the interference pattern 6, and an X-ray detector 5 that detects an intensity distribution of the X-rays from the analyzer grating 24. The X-ray Talbot interferometer 300 according to this embodiment may further include the X-ray source 31, or the X-ray source 31 may be separate from the X-ray Talbot interferometer 300. Similarly to the first embodiment, the beam splitter grating 3 and the analyzer grating 24 have patterns illustrated in FIGS. 2B and 2C, respectively, which are not described herein. The values of the distances $L_{S1}$ and $L_{12}$ are also similar to the corresponding values in the Talbot interferometer according to the first embodiment and the Talbot interferometer of the related art.

In the following, the effect produced when the grating period $d_2$ of the analyzer grating has a different value from the value of the period $d_{IP}$ of the interference pattern in this embodiment will be described with a simple model.

First, the grating period $d_2$ of the analyzer grating 24 in this embodiment is represented by the following equation using a rate of deviation $\alpha_2$ from $d_{IP}$:

[Math. 50]

$$d_2 = n_2 d_{IP}(1+\alpha_2). \quad (49)$$

The rate of deviation $\alpha_2$ may also take a negative value, where $\alpha_2 \neq 0$. When $\alpha_2$ is equal to 0, the design conditions of the analyzer grating are the same as those in Comparative Example 2. In a typical Talbot-Lau interferometer and the Talbot interferometer according to the first embodiment, $d_{2C}$ may be an integer multiple of $d_{IPC}$. Also in this embodiment, $d_2$ may be an integer multiple of 2 or more of $d_{IP}$ with a certain rate of deviation. In this case, $n_2$ takes an integer greater than or equal to 2. However, the above-described configuration has a drawback in that the overall X-ray transmittance of the analyzer grating is reduced, which is generally not preferable. Thus, preferably, $n_2$ is equal to 1. In the following, a description will be given of the case where $d_2$ has a slight rate of deviation $\alpha_2$ from $d_{IP}$ (i.e., $n_2=1$) as an example.

Next, the coordinate system (x, y) is taken on the analyzer grating, and the periodic direction of the interference pattern is assumed to coincide with the x-axis direction. The coordinate system (x, y) may not necessarily be the same as the coordinate system (x, y) in the first embodiment.

When the X-ray source is minute, and can be regarded as a single point, similarly to $g_{IPo}$ in Expression (2), the intensity distribution $g_{IP}(x, y)$ of the interference pattern on the analyzer grating can be expressed by

[Math. 51]

$$g_{IP}(x, y) = a(x, y) + b(x, y)\cos\left[\frac{2\pi}{d_{IP}} + \phi(x, y)\right]. \quad (50)$$

Using Expression (3), Expression (50) can be rewritten as

[Math. 52]

$$g_{IP}(x, y) = a(x, y) + \frac{1}{2}c(x, y)e^{i\frac{2\pi}{d_{IP}}x} + \frac{1}{2}c^*(x, y)e^{-i\frac{2\pi}{d_{IP}}x}. \quad (51)$$

Applying the two-dimensional Fourier transform to both sides yields

[Math. 53]

$$G_{IP}(\xi, \eta) = A(\xi, \eta) + \frac{1}{2}C\left(\xi - \frac{1}{d_{IP}}, \eta\right) + \frac{1}{2}C^*\left(\xi + \frac{1}{d_{IP}}, \eta\right), \quad (52)$$

where $\xi$ represents the spatial frequency in the x-axis direction, and $\eta$ represents the spatial frequency in the y-axis direction.

Next, consideration will be given to an X-ray intensity distribution which is finally measured with the X-rays transmitted through the analyzer grating and incident on the X-ray detector. As described in the first embodiment, a transmittance distribution $t_2(x, y)$ of the analyzer grating is represented by

[Math. 54]

$$t_2(x, y) = 1 + \cos\left(\frac{2\pi}{d_2}x - \phi_r\right), \quad (53)$$

where $\phi_r$ denotes the phase of the analyzer grating (corresponding to the x-direction position of the grating). In general, the analyzer grating is placed in close vicinity of the detection surface of the X-ray detector. Thus, the analyzer grating and the detection surface are approximated as being in the same position. Similarly to the first embodiment, if the point spread function (PSF) specific to intensity distribution measurement performed by the X-ray detector used is represented by $h_D(x, y)$, the X-ray intensity distribution $g_M(x, y)$, which is finally measured, is given by

[Math. 55]

$$g_M(x,y) = [g_{IP}(x,y)t_2(x,y)] * h_D(x,y). \quad (54)$$

Accordingly, $G_M(\xi, \eta)$, which is the Fourier transform of $g_M(x, y)$, can be expressed by the following equation using Expressions (52) to (54):

[Math. 56]

$$G_M(\xi, \eta) = [G_{IP}(\xi, \eta) * T_2(\xi, \eta)] \quad (55)$$

$$H_D(\xi, \eta) \approx \left[A(\xi, \eta) + \frac{1}{4}C\left(\xi - \frac{1}{d_{IP}} + \frac{1}{d_2}, \eta\right)e^{i\phi_r} + \frac{1}{4}C^*\left(\xi + \frac{1}{d_{IP}} - \frac{1}{d_2}, \eta\right)e^{-i\phi_r}\right]H_D(\xi, \eta).$$

Here, a term in which the center of the function is located in a region that is very far from the origin in the ($\xi$, $\eta$) space is considered to have a sufficiently small value when filtered with $H_D(\xi, \eta)$, and is ignored. Further, $|H_D(\xi, \eta)|$ is a function corresponding to the modulation transfer function (MTF) of the detector. In the manner described above, it will be understood that the analyzer grating has a function to perform spatial-frequency shifting of information on the interference pattern to make information of a certain spatial frequency band of the interference pattern detectable by moving the frequency band to a range within which $H_D(\xi, \eta)$ has a dominantly larger value than zero.

In this case, the center frequency of the spatial frequency band to be made detectable is located at $(\xi, \eta) = (1/d_2, 0)$ on the positive side of the $\xi$ axis.

The following description will be given taking as an example the case where intensity distribution measurement is performed three times with $\phi_r$ changed, and predetermined computation based on the principle of the so-called phase shift method is performed to acquire information on the intensity distribution $g_M(x, y, k)$ and its Fourier transform, that is, $G_M(\xi, \eta, k)$ (where k=1, 2, 3). If $\phi_r$ is changed in the manner given by

[Math. 57]

$$\phi_r(k) = 0.2\pi/3.4\pi/3 (k=1,2,3), \quad (56)$$

then, restored values $A_R(\xi, \eta)$ and $C_R(\xi, \eta)$ of $A(\xi, \eta)$ and $C(\xi, \eta)$, which are sample information expressed in the frequency domain, can be calculated in accordance with

[Math. 58]

$$A_R(\xi, \eta) = \frac{1}{3}\sum_{k=1}^{3} G_M(\xi, \eta, k) \quad (57)$$

$$= A(\xi, \eta)H_D(\xi, \eta)$$

[Math. 59]

$$C_R(\xi, \eta) = \frac{1}{3}\sum_{k=1}^{3} G_M\left(\xi + \frac{1}{d_{IP}} - \frac{1}{d_2}, \eta, k\right)e^{-i\frac{2\pi}{3}(k-1)} \quad (58)$$

$$= \frac{1}{4}C(\xi, \eta)H_D(\xi - \xi_2, \eta),$$

respectively. As in Expression (22), $\xi_2$ is given by

[Math. 60]

$$\xi_2 = \frac{1}{d_2} - \frac{1}{d_{IP}}. \quad (59)$$

As is seen from Expressions (57) and (58), the sample information restored by the above-described technique is finally influenced by the frequency filter $H_D$. As is also seen from Expression (57), $A_R(\xi, \eta)$ (and $a_R(x, y)$, which is expressed in the (x, y) space), which is acquired, is not affected by the grating period of the analyzer grating since the center position of $A(\xi, \eta)$, which is the spectrum of sample information, and the center position of $H_D$ to be applied to $A(\xi, \eta)$ always match.

As is seen from Expression (58), in contrast, for $C_R(\xi, \eta)$ (and $c_R(x, y)$, which is expressed in the (x, y) space), which is acquired, the center position of $C(\xi, \eta)$, which is the spectrum of sample information, and the center position of the frequency filter $H_D$ to be applied to $C(\xi, \eta)$ do not always match. The relative amount of displacement of the filter is determined in accordance with the relationship between the grating period $d_2$ of the analyzer grating and the period $d_{IP}$ of the interference pattern. Specifically, the amount of displacement $\xi_2$ of the filter $H_D$ with respect to $C(\xi, \eta)$ is determined in accordance with the difference between $1/d_2$ and $1/d_{IP}$. Thus, the adjustment of the value $d_2$ enables control of the influence of the frequency filter $H_D$. The Talbot interferometer of the related art, which is the Talbot interferometer according to Comparative Example 2, is generally designed to meet $d_2 = d_{IP}$. Thus, $\xi_2 = 0$ is established.

Next, a difference between the Talbot interferometer according to this embodiment and the Talbot interferometer according to Comparative Example 2 will be described using simulation results. The Talbot interferometer according to Comparative Example 2 corresponds to the Talbot interferometer according to this embodiment when the rate of deviation $\alpha_2$ for the grating period is zero. Thus, performance comparison can be made through simulation using formulas similar to those in this embodiment. That is, the Talbot interferometer according to Comparative Example 2 is an interferometer designed to satisfy $d_2 = d_{IP}$. Furthermore, it is assumed here that the function $h_D(x, y)$ is a two-dimensional Gaussian-shaped function.

Also in a simulation for comparison between the Talbot interferometer according to this embodiment and the Talbot interferometer according to Comparative Example 2, similarly to the simulation in the first embodiment, the images illustrated in FIGS. 9A and 9B were used.

Figure 20A:
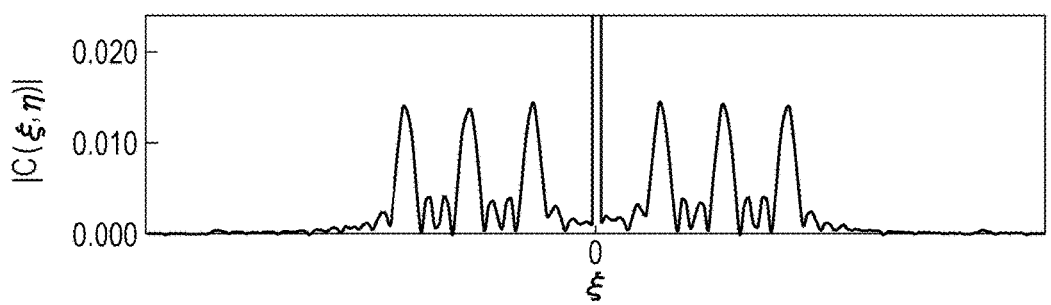
FIGS. 20A to 20C illustrate an example of spectra of sample information restored in Comparative Example 2.
Figure 20B:
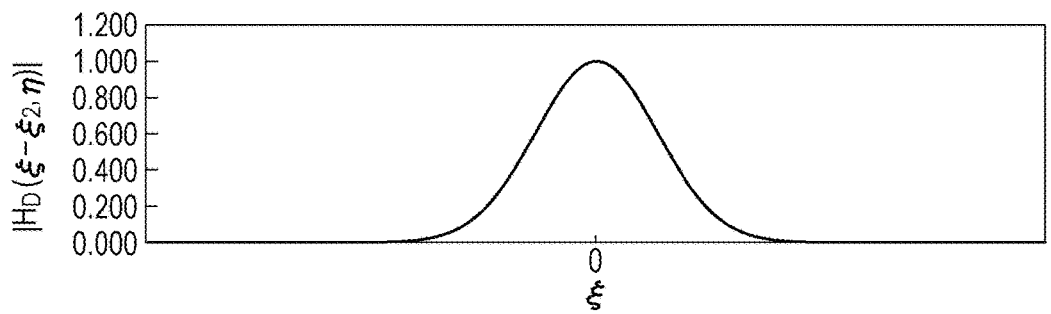
Figure 20C:
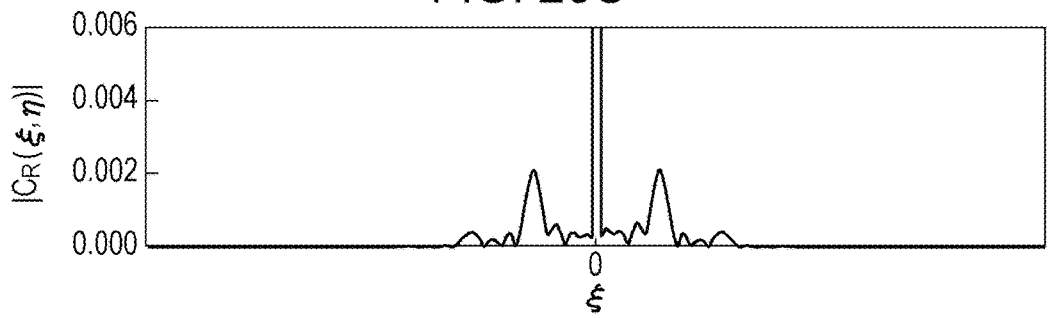

FIGS. 20A, 20B, and 20C depict the results of simulation of all the steps of calculating a restored value $C_R(\xi, \eta)$ of sample information by using the phase shift method as described above in a Talbot-Lau interferometer of the related art, which is the Talbot interferometer according to Comparative Example 2. FIGS. 20A, 20B, and 20C depict the profiles of $|C(\xi, \eta)|$, $|H_D(\xi-\xi_2, \eta)|$, and $|C_R(\xi, \eta)|$ on the $\xi$ axis, respectively. As described above, the center frequency of the spatial frequency band to be made detectable by the effect of the analyzer grating is located at $(\xi, \eta) = (1/d_2, 0)$ on the positive side of the $\xi$ axis. Thus, in the Talbot interferometer according to Comparative Example 2 with $d_2 = d_{IP}$, the center frequency of the detected band is the component at $(\xi, \eta) = (1/d_{IP}, 0)$, and matches the carrier. Further, $C(\xi-1/d_{IP}, \eta)$, which is the spectrum of sample information, is distributed as sidebands centered at the carrier. In this case, as illustrated in FIG. 20B, a local maxima of the frequency filter $H_D(\xi-\xi_2, \eta)$ matches the center of $C(\xi, \eta)$. Thus, components in a region farther from the origin in $C(\xi, \eta)$ are largely lost during transmission. In other words, high-frequency components in c(x, y) are largely lost.

Figure 21A:
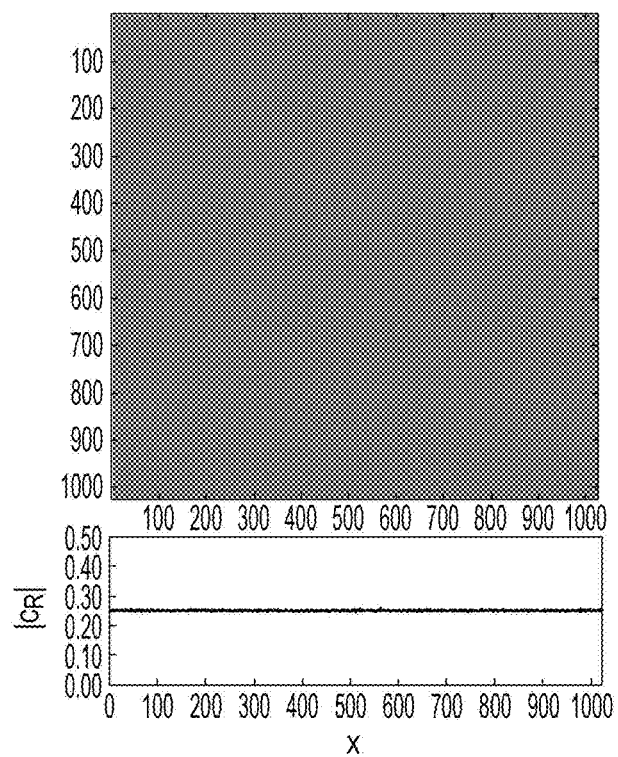
FIGS. 21A and 21B illustrate an example of sample information restored in Comparative Example 2.
Figure 21B:
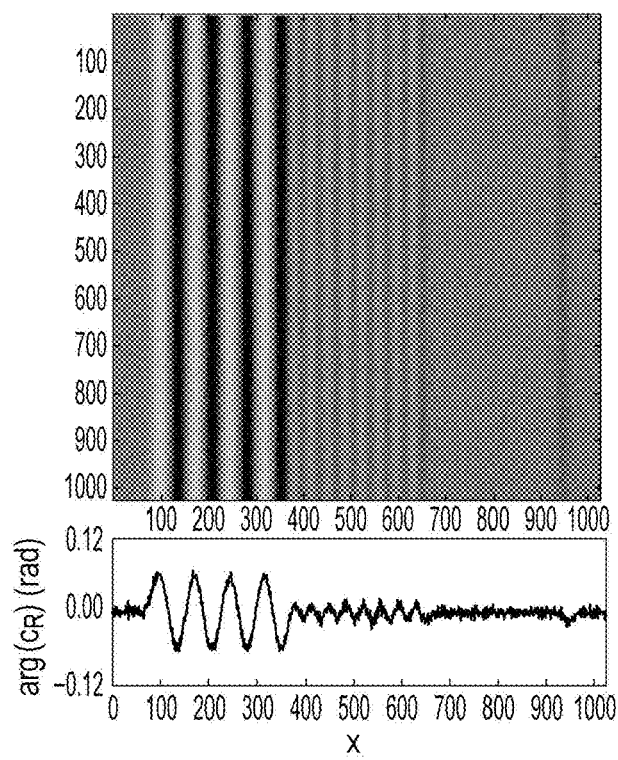

FIGS. 21A and 21B illustrate $c_R(x, y)$ obtained as a result of simulation and corresponding profiles on the x axis. FIGS. 21A and 21B illustrate $|c_R(x, y)|$ and $\arg[c_R(x, y)]$, respectively. In this simulation, a certain amount of noise is added. As is anticipated from the change in spectrum described above, comparing FIGS. 21A and 21B with FIGS. 9A and 9B shows that high-frequency components (components appearing in the right portion of the figures) apparently attenuate in the image and the signal-to-noise ratio decreases, resulting in a difficulty in detection.

Figure 17A:
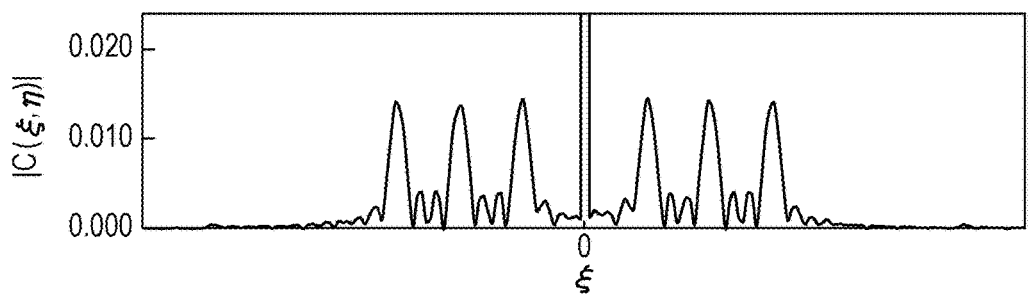
FIGS. 17A to 17C illustrate an example of spectra of sample information restored in the second embodiment.
Figure 17B:
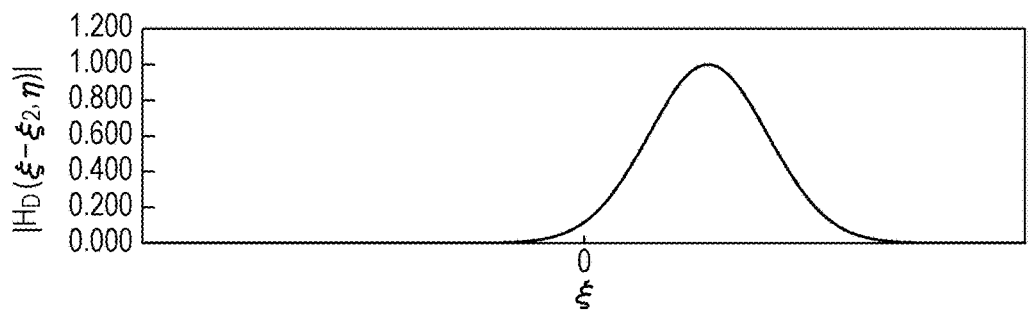
Figure 17C:
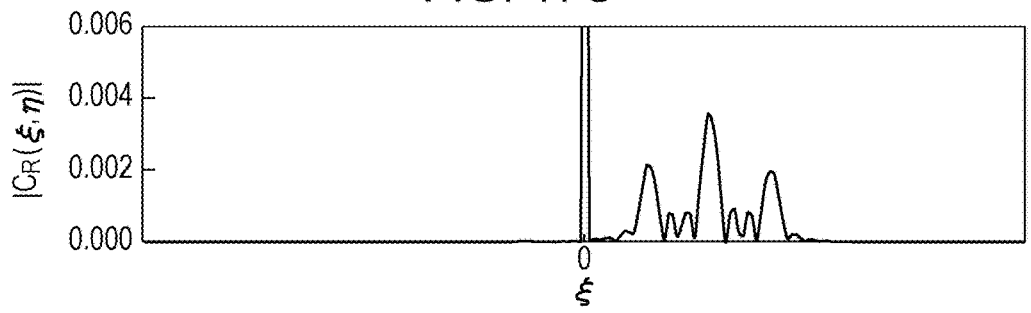

FIGS. 17A, 17B, and 17C illustrate the results of simulation of the steps of calculating a restored value $C_R(\xi, \eta)$ of sample information in the Talbot interferometer according to this embodiment by using the phase shift method. FIGS. 17A, 17B, and 17C depict the profiles of $|C(\xi, \eta)|$, $|H_D(\xi-\xi_2, \eta)|$, and $|C_R(\xi, \eta)|$ on the $\xi$ axis, respectively. In the Talbot interferometer according to this embodiment, $d_2 \neq d_{IP}$ is established. Thus, the center frequency of the band detected by the detector does not match the carrier, and is a frequency component in a sideband including the sample information. In this case, as illustrated in FIG. 17B, a local maxima of the frequency filter $H_D(\xi-\xi_2, \eta)$ and the center of $C(\xi, \eta)$ do not match, and a displacement of $\xi_2$ occurs between them. Accordingly, here, only the components in the region of $\xi > 0$ in $C(\xi, \eta)$ are substantially transmitted (FIG. 17C). Comparing the result with the shape of $|C_R(\xi, \eta)|$ in Comparative Example 2 illustrated in FIG. 20C shows that a larger amount of components in a region farther from the origin in $C(\xi, \eta)$ are transmitted. In other words, a larger amount of high-frequency components in c(x, y) remain.

Figure 18A:
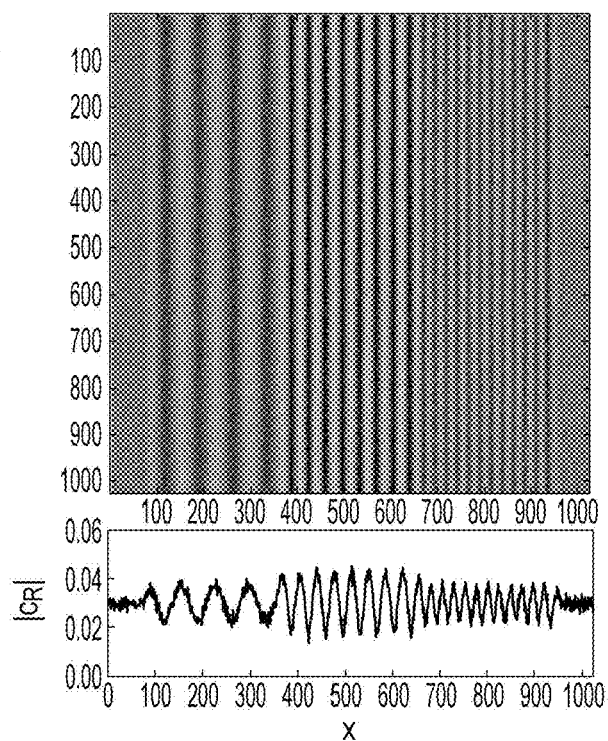
FIGS. 18A and 18B illustrate an example of sample information restored in the second embodiment.
Figure 18B:
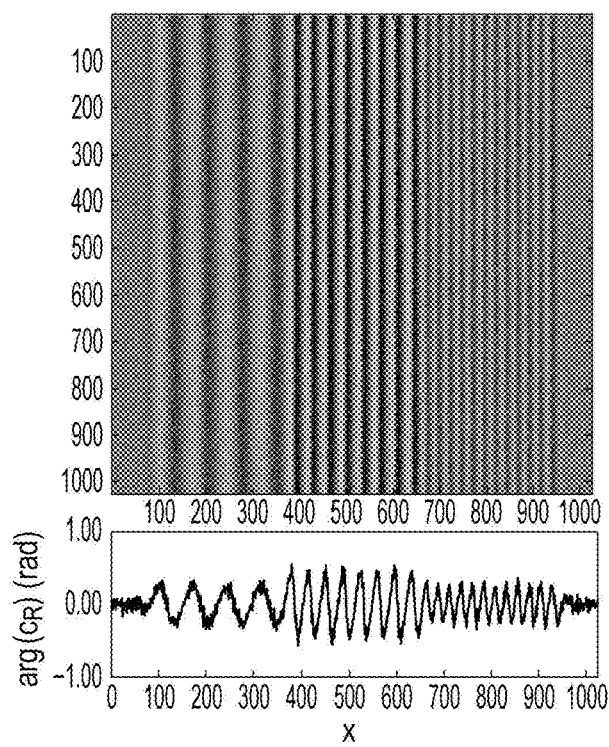

FIGS. 18A and 18B illustrate $c_R(x, y)$ obtained as a result of simulation and corresponding profiles on the x axis. FIGS. 18A and 18B illustrate $|c_R(x, y)|$ and $\arg[c_R(x, y)]$, respectively. Also in this simulation, an equivalent amount of noise to that in Comparative Example 2 is added. As is anticipated from the change in spectrum described above, comparing FIGS. 18A and 18B with FIGS. 21A and 21B and FIGS. 9A and 9B shows that a larger amount of high-frequency components than those in Comparative Example 2 remain in the image and the capability of detecting high-frequency components is improved. In FIG. 18A, a sample image that is not shown in FIG. 9A appears because, due to the effect of asymmetry of the frequency filter $H_D(\xi-\xi_2, \eta)$ with respect to the center of $C(\xi, \eta)$, information on $\phi(x, y)$ also appears on the absolute-value side of $c_R(x, y)$. Likewise, although not shown in this simulation, this embodiment has a secondary effect that information on b(x, y) also appears on the argument side of $c_R(x, y)$.

Next, consideration will be given to a preferred range of the value $d_2$ in this embodiment.

First, as in the simulation, it is assumed that $h_D(x, y)$, which is the point spread function specific to the X-ray detector, has a two-dimensional Gaussian shape. In this case, as given in Expression (30), $h_D(x, y)$ can be expressed by

[Math. 61]

$$h_D(x, y) \propto e^{-\frac{x^2+y^2}{2\sigma_D^2}}, \quad (60)$$

where $\sigma_D$ is a constant that defines the width of $h_D(x, y)$. In this case, if coefficients are ignored, $H_D(\xi, \eta)$, which is the Fourier transform of $h_D(x, y)$, can be expressed by

[Math. 62]

$$H_D(\xi, \eta) = e^{-\frac{\xi^2+\eta^2}{2\sigma_{DF}^2}}, \tag{61}$$

where $\sigma_{DF}$ is a constant that defines the width of $H_D(\xi, \eta)$, and is given by

[Math. 63]

$$\sigma_{DF} = \frac{1}{2\pi\sigma_D}. \tag{62}$$

Further, the amount of displacement $\xi_2$ between the center of the spectrum $C(\xi, \eta)$ of sample information and the local maxima of the frequency filter $H_D(\xi-\xi_2, \eta)$ can be expressed by the following equation (where $|\alpha_2| \ll 1$):

[Math. 64]

$$\xi_2 = \frac{1}{d_2} - \frac{1}{d_{IP}} = -\frac{1}{d_{IP}} \frac{\alpha_2}{1+\alpha_2} \approx -\frac{\alpha_2}{d_{IP}}. \tag{63}$$

Meanwhile, $C(\xi, \eta)$, which is the spectrum of sample information, is two-dimensionally distributed around the origin. As described above, $\phi(x, y)$ reflects the distribution obtained by differentiation of the phase distribution of X-rays that have propagated through the sample in the direction of the carrier. Accordingly, the component $C(\xi, \eta)$ distinctly appears particularly in the $\xi$-axis direction that is the direction of the carrier. It is thus preferable that the local maxima of the filter $H_D$ be shifted along the $\xi$ axis. In other words, it is preferable that the periodic direction of the interference pattern and the periodic direction of the analyzer grating match. Making $|\xi_2|$ large enables the transmission of a large amount of higher frequency components in $c(x, y)$, and also causes a drawback in that the absence of low-frequency components will result in an unnatural image. In order to achieve the effect of increasing the amount of transmission of high-frequency components while preventing the absence of low-frequency components, similarly to Expression (40), it may be sufficient to select $\xi_2$ so as to satisfy

[Math. 65]

$$0.5\sigma_{DF} < |\xi_2| < 3.0\sigma_{DF}. \tag{64}$$

Letting the full width at half maximum of $h_S(x, y)$ be $w_D$, the relationship of $w_D = 2\sigma_D(2\ln 2)^{0.5}$ is established when $h_S(x, y)$ has a Gaussian shape. Thus, Expression (64) can be rewritten as

[Math. 66]

$$0.5\frac{\sqrt{2\ln 2}}{\pi w_D} < |\xi_2| < 3.0\frac{\sqrt{2\ln 2}}{\pi w_D}. \tag{65}$$

Calculating the coefficient portions and rewriting Expression (65) with $\alpha_2$ yields

[Math. 67]

$$0.2\frac{d_{IP}}{w_D} < |\alpha_2| < 1.1\frac{d_{IP}}{w_D}. \tag{66}$$

Letting the grating period of the beam splitter grating be $d_1$, the relationship between $d_{IP}$ and $d_1$ can generally be expressed by

[Math. 68]

$$d_{IP} = \frac{d_1}{m} \frac{L_{S1} + L_{12}}{L_{S1}}, \tag{67}$$

where m is a positive integer. The preferred value of m is determined in accordance with the relationship between the pattern of the beam splitter grating and the interference pattern, and, in general, it is preferable to set m=1 or 2. A typical example in a case where it is preferable to set m=1 is the use of the so-called $\pi/2$-modulation phase grating as the beam splitter grating. A typical example in a case where it is preferable to set m=2 is the use of the so-called $\pi$-modulation phase grating as the beam splitter grating. Also when the harmonic components in the interference pattern are used as the carrier, m takes a value other than 1. Using Expression (67), Expression (66) can be rewritten with $d_1$ as

[Math. 69]

$$0.2\frac{d_1}{mw_D}\frac{L_{S1}+L_{12}}{L_{S1}} < |\alpha_2| < 1.1\frac{d_1}{mw_D}\frac{L_{S1}+L_{12}}{L_{S1}}. \tag{68}$$

Expression (68) is an expression that gives a preferred range of the value $\alpha_2$ when taking into account the point spread function specific to the detector. In this case, the value $d_2$ can be rewritten with $d_1$ as

[Math. 70]

$$d_2 = \frac{n_2 d_1}{m}\frac{L_{S1}+L_{12}}{L_{S1}}(1+\alpha_2). \tag{69}$$

The method for measuring the point spread function specific to the detector is well known, and the value $w_D$, which is the full width at half maximum of the point spread function specific to the detector, can be easily measured. Examples of the simple method include measurement based on a result of imaging with a pinhole placed at a position that is in close proximity to the detection surface of the detector. Accordingly, it is easy to verify whether or not the interferometer satisfies the conditions in Expressions (68) and (69).

While the foregoing description has been made taking as an example an interferometer that does not include a source grating, the Talbot interferometer according to this embodiment may include a source grating. In this case, $L_{S1}$ in Expressions (68) and (69) denotes the distance between the source grating and the beam splitter grating. As in the first embodiment, the source grating may be configured such that bright portions of interference patterns overlap each other with a displacement therebetween and dark portions of the interference patterns overlap each other with a displacement therebetween (i.e., $\alpha_1 \neq 0$), or may be a source grating used in the Talbot-Lau interferometer of the related art (i.e., $\alpha_1 = 0$).

It may be likely that setting the value $|\alpha_2|$ to be comparatively large will result in a reduction in the quality of an image when $c_R(x, y)$ is displayed as an image because of a significantly small value of the carrier component. To address this issue, similarly to the first embodiment, the following process may be performed: The component corresponding to the carrier is numerically restored, and the restored value is added to the calculated function $c_R(x, y)$. For imaging of $c_R(x, y)$, which is a complex-valued distribution function, imaging by mapping the real part and the imaginary part may be performed, for example, instead of, as described above by way of example, imaging by mapping the absolute value and the argument.

In the foregoing description, the simulation used is based on the assumption that, among the sidebands in $G_{IP}(\xi, \eta)$, components in the upper sideband are transmitted by setting $\alpha_2 < 0$. Components in the lower sideband may be transmitted by setting $\alpha_2 > 0$. As described above, depending on the type of the sample, selection of the upper or lower sideband for transmission might cause large differences in the visibility of the structure of the sample or in detection performance. Accordingly, in view of the above-described relationships, it is more preferable to predict in advance the feature of the sideband which will be produced due to the influence of the sample and to reflect the feature to the setting of the value $\xi_2$. In addition, similarly to the first embodiment, a configuration which allows a user to set the frequency that the user particularly wishes to observe may be used.

Similarly to the first embodiment, furthermore, in order to effectively improve spatial resolution, it is preferable to use a measurement technique that is based on obtaining a moiré image a plurality of times, such as a phase shift method.

Furthermore, similarly to the first embodiment, a displacement of $\xi_2$ occurs between the center of the spectrum $G_M(\xi, \eta, k)$ of the X-ray intensity distribution acquired by the detector and the center of the spectrum C of sample information. The displacement between the centers of the spectra may be corrected by frequency shifting in a computer, or may be corrected by performing division operation by reference data. In addition, the center of $C_R$ is shifted in the frequency coordinate system, causing the entire $C_R$ to lie beyond a detection spatial frequency band inherent in the detector. To address this potential situation, preferably, a frequency band wider than the inherent detection spatial frequency band of the detector is prepared in the computer, and $C_R$ is contained within the frequency band so that the center of $C_R$ matches the origin of the frequency coordinate system. In other words, preferably, the data interval of image data corresponding to $c_R(x, y)$ that the interferometer system displays or records is set to be smaller than the inherent pixel pitch of the detector.

Hereinafter, more specific examples of the first and second embodiments will be described.

EXAMPLE 1

Example 1 is a specific example of the first embodiment. An X-ray tube is used as an X-ray source. The anode of the X-ray tube is made of tungsten. With the adjustment with a tube voltage or a filter, the energy spectrum of X-ray radiation exhibits a substantial local maxima at a position of 22 keV. Further, the effective light emission intensity distribution of the focal spot of the X-ray tube has a two-dimensional Gaussian shape with a full width at half maximum of 300 μm. The patterns of the source grating, the beam splitter grating, and the analyzer grating are similar to those illustrated in FIGS. 2A, 2B, and 2C, respectively. The beam splitter grating is a silicon phase grating, and the grating period $d_1$ is equal to 12.00 μm. The difference between the phase-advancing portions and phase-delaying portions of the beam splitter grating is implemented by a difference in the thickness of the silicon substrate, and the beam splitter grating is designed to apply a phase difference of $\pi$ rad to 22-keV X-rays that have been transmitted therethrough. Further, the source grating and the analyzer grating are fabricated by forming a gold plated film with a thickness of 100 μm on a silicon substrate as an X-ray shielding portion.

In Example 1, the distances $L_{01}$ and $L_{12}$ are equal to 1000.0 mm and 469.3 mm, respectively. In this case, 22 keV X-rays emitted from a single point on the source grating are diffracted by the periodic structure of the beam splitter grating, thereby forming a high-visibility interference pattern at the same position as that of the analyzer grating due to the Talbot effect. The distance $L_{S0}$ between the X-ray emission spot and the source grating is set to 100.0 mm.

In this case, the grating period $d_0$ of the source grating calculated by Expression (46) is given by $d_0 = 18.785 (1+\alpha_1)$ μm if the conditions of $n_1 = 1$ and $m = 2$ are selected. On the other hand, a preferred range of the value $|\alpha_1|$ is calculated in accordance with Expression (44) (when $w_S$ is corrected by taking into account the presence of $L_{S0}$) to obtain $0.010 < |\alpha_1| < 0.152$. In Example 1, furthermore, if the condition of $|\xi_0| \approx 2\sigma_{SF}$ is selected, it may be sufficient that $|\alpha_1| = 0.052$. In Example 1, therefore, $\alpha_1$ being positive is selected, and $d_0 = 19.755$ μm is set.

Further, the grating period $d_2$ of the analyzer grating is set to 9.271 μm in accordance with Expression (47) (where $n_2 = 1$ and $\alpha_1 = 0.052$). The X-ray detector is a flat panel detector with a pixel pitch of 50 μm, and is placed in close proximity to the analyzer grating. When imaging is performed, $c_R(x, y)$, which is a restored value of sample information, is acquired using a phase shift method that is based on scanning over the beam splitter grating.

EXAMPLE 2

Example 2 is a specific example of the first embodiment. The interferometer includes, as an X-ray source, an X-ray tube having a tungsten anode. By adjusting a tube voltage or a filter, the X-ray tube emits X-rays with a certain energy bandwidth centered at a photon energy of approximately 25 keV from a radiation aperture. The interferometer is designed to effectively act particularly on X-rays (with a photon energy of approximately 25 keV) having a wavelength of approximately 0.05 nm. The effective light emission intensity distribution of the X-ray emission spot has a two-dimensional Gaussian shape with a full width at half maximum of 500 μm. The patterns of the source grating, the beam splitter grating, and the analyzer grating are illustrated in FIGS. 2A, 2B, and 2C, respectively. The beam splitter grating is a silicon phase grating, and the grating period $d_1$ is equal to 8.0 μm. The beam splitter grating has a difference of 32 μm in the thickness of the grating substrate between the phase-advancing portions and the phase-delaying portions, thereby applying a phase modulation of approximately $\pi$ rad to incident X-rays having a wavelength of approximately 0.05 nm. The phase-advancing portions and the phase-delaying portions have an equal width. The source grating and the analyzer grating have a structure in which a gold plated film with a thickness of 100 μm is formed as an X-ray shielding portion on a silicon substrate. The X-ray detector is a flat panel detector with a pixel pitch of 50 µm. The point spread function specific to the detector has a two-dimensional Gaussian shape with a full width at half maximum of 100 µm.

The distances $L_{01}$ and $L_{12}$ are equal to 800 mm and 200 mm, respectively. The source grating and the X-ray emission spot are placed substantially at the same position, and the analyzer grating and the detection surface of X-ray detector are placed substantially at the same position. In this case, the values $d_0$ and $d_2$ are calculated by 20.0 $(1+\alpha_1)$ µm and 5.0 $(1+\alpha_1)$ µm in accordance with Expressions (46) and (47), respectively. Here, m=2 and $n_1=n_2=1$ are set by taking into account that the beam splitter grating is a so-called π-modulation grating. In Example 2, the rate of deviation $\alpha_1$ is set to −0.020. That is, $d_0$ is equal to 19.6 µm and $d_2$ is equal to 4.9 µm. In this case, preferred ranges of the value $\alpha_1$ are $0.008<|\alpha_1|<0.044$ and $0.006<|\alpha_1|<0.034$ according to Expression (44) and Expression (45), respectively. When a sample image is to be captured, $c_R(x, y)$, which is a restored value of sample information, is calculated using a phase shift method that is based on scanning over the analyzer grating.

EXAMPLE 3

Example 3 is a specific example of the second embodiment. Unlike Example 2, an interferometer does not include a source grating but includes an X-ray source having an X-ray emission spot with an effective size of 10 µm.

Similarly to Example 2, the interferometer is also designed to effectively act particularly on X-rays (with a photon energy of approximately 25 keV) having a wavelength of approximately 0.05 nm. The structures of the beam splitter grating and the analyzer grating are similar to those in Example 2, and are not described herein. The X-ray detector is a flat panel detector with a pixel pitch of 80 µm. The point spread function specific to the detector has a two-dimensional Gaussian shape with a full width at half maximum of 160 µm.

The distances $L_{S1}$ and $L_{12}$ are equal to 800 mm and 200 mm, respectively. The analyzer grating and the detection surface of X-ray detector are placed substantially at the same position. In this case, the value $d_2$ is calculated by 5.0 $(1+\alpha_2)$ µm in accordance with Expression (49). Here, m=2 and $n_2=1$ are set by taking into account that the beam splitter grating is a so-called π-modulation grating. In Example 3, the rate of deviation $\alpha_2$ is set to −0.020. That is, the value $d_2$ is equal to 4.9 µm. In this case, a preferred range of the value $\alpha_2$ is $0.006<|\alpha_2|<0.034$ according to Expression (68). When a sample image is to be captured, $c_R(x, y)$, which is a restored value of sample information, is calculated using a phase shift method that is based on scanning over the analyzer grating.

Other Embodiments

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-026677, filed Feb. 14, 2014, which is hereby incorporated by reference herein in its entirety.

The invention claimed is:

1. An X-ray Talbot interferometer comprising:
a source grating including a plurality of X-ray transmitting portions, configured to allow some of X-rays from an X-ray source to pass therethrough;
a beam splitter grating having a periodic structure, configured to diffract X-rays from the X-ray transmitting portions by using the periodic structure to form interference patterns each corresponding to one of the plurality of X-ray transmitting portions; and
an X-ray detector configured to detect X-rays from the beam splitter grating,
wherein the plurality of X-ray transmitting portions are arranged so that each of the interference patterns are superimposed on one another to enhance a specific spatial frequency component, the interference patterns being superimposed on one another while displaced by a distance that is different from a pattern period of each of the interference patterns, and
wherein the specific spatial frequency component is a spatial frequency component in a sideband generated by modulation of spatial frequency components specific to the interference patterns by a sample.

2. An X-ray Talbot interferometer comprising:
a source grating including a plurality of X-ray transmitting portions, configured to allow some of X-rays from an X-ray source to pass therethrough;
a beam splitter grating having a periodic structure, configured to diffract X-rays from the X-ray transmitting portions by using the periodic structure to form interference patterns each corresponding to one of the plurality of X-ray transmitting portions, each of the interference patterns being superimposed on another interference pattern while displaced by a distance that is different from a pattern period of each of the interference patterns; and
an X-ray detector configured to detect X-rays from the beam splitter grating,
wherein the plurality of X-ray transmitting portions of the source grating have a pitch $d_0$ which is represented by $$d_0 = \frac{n_1 d_1}{m} \frac{L_{01} + L_{12}}{L_{12}} (1 + \alpha_1),$$

where $d_1$ denotes a grating period of the beam splitter grating, $n_1$ and m are positive integers, $L_{01}$ denotes a distance between the source grating and the beam splitter grating, $L_{12}$ denotes a distance between the beam splitter grating and a detection surface of the X-ray detector or a distance between the beam splitter grating and an analyzer grating placed between the beam splitter grating and the detection surface of the X-ray detector, and $\alpha_1$ denotes a constant in a range of $$6.2 \frac{d_1}{m w_S} \frac{L_{01} + L_{12}}{L_{12}} < |\alpha_1| < 1.1 \frac{d_1}{m w_S} \frac{L_{01} + L_{12}}{L_{12}},$$

where $w_S$ denotes a full width at half maximum of a light emission intensity distribution of an X-ray emission spot in the X-ray source.

3. The X-ray Talbot interferometer according to claim 2, further comprising an analyzer grating configured to shield a portion of the interference pattern,
wherein the X-ray detector detects X-rays from the analyzer grating.

4. An X-ray Talbot interferometer comprising:
a source grating including a plurality of X-ray transmitting portions, configured to allow some of X-rays from an X-ray source to pass therethrough;
a beam splitter grating having a periodic structure, configured to diffract X-rays from the X-ray transmitting portions by using the periodic structure to form interference patterns each corresponding to one of the plurality of X-ray transmitting portions, each of the interference patterns being superimposed on another interference pattern while displaced by a distance that is different from a pattern period of each of the interference patterns;

an analyzer grating configured to shield a portion of the interference pattern; and an X-ray detector configured to detect X-rays from the analyzer grating, wherein the plurality of X-ray transmitting portions of the source grating have a pitch $d_0$ and the analyzer grating has a grating period $d_2$, the pitch $d_0$ and the grating period $d_2$ being represented by $$d_0 = \frac{n_1 d_1}{m} \frac{L_{01} + L_{12}}{L_{12}} (1 + \alpha_1)$$

and $$d_2 = \frac{n_2 d_1}{m} \frac{L_{01} + L_{12}}{L_{01}} (1 + \alpha_1),$$

respectively, where $d_1$ denotes a grating period of the beam splitter grating, $n_1$ and $m$ are positive integers, $L_{01}$ denotes a distance between the source grating and the beam splitter grating, $L_{12}$ denotes a distance between the beam splitter grating and the analyzer grating, and $\alpha_1$ denotes a constant in a range of $$0.2 \frac{d_1(L_{01} + L_{12})}{m\sqrt{(w_S L_{12})^2 + (w_D L_{01})^2}} < |\alpha_1| < 1.1 \frac{d_1(L_{01} + L_{12})}{m\sqrt{(w_S L_{12})^2 + (w_D L_{01})^2}}$$

where $w_S$ denotes a full width at half maximum of a light emission intensity distribution of an X-ray emission spot in the X-ray source, and $w_D$ denotes a full width at half maximum of a point spread function specific to the X-ray detector.

5. An X-ray Talbot interferometer comprising:
a beam splitter grating having a periodic structure, configured to diffract X-rays from an X-ray source by using the periodic structure to form an interference pattern;
an analyzer grating configured to shield a portion of the interference pattern; and
an X-ray detector configured to detect X-rays from the analyzer grating,
wherein the analyzer grating performs spatial-frequency shifting of information on the interference pattern to make information on a spatial frequency band of the interference pattern detectable by the X-ray detector, and
wherein the analyzer grating has a grating period which is different from a pattern period of the interference pattern so as to center the spatial frequency band on a spatial frequency component in a sideband produced by a spatial frequency component specific to the interference pattern being modulated by a sample.

6. An X-ray Talbot interferometer comprising:
a beam splitter grating having a periodic structure, configured to diffract X-rays from an X-ray source by using the periodic structure to form an interference pattern;
an analyzer grating configured to shield a portion of the interference patterns; and, wherein the interference patterns are superimposed on one another while displaced by a distance that is different from a pattern period of the interference patterns;
an X-ray detector configured to detect X-rays from the analyzer grating,
wherein the analyzer grating has a grating period $d_2$ which is represented by $$d_2 = \frac{n_2 d_1}{m} \frac{L_{S1} + L_{12}}{L_{S1}} (1 + \alpha_2),$$

where $d_1$ denotes a grating period of the beam splitter grating, $n_2$ and $m$ are positive integers, $L_{S1}$ denotes a distance between the X-ray source and the beam splitter grating, $L_{12}$ denotes a distance between the beam splitter grating and the analyzer grating, and $\alpha_2$ denotes a constant in a range of $$0.2 \frac{d_1}{m w_D} \frac{L_{S1} + L_{12}}{L_{S1}} < |\alpha_2| < 1.1 \frac{d_1}{m w_D} \frac{L_{S1} + L_{12}}{L_{S1}},$$

where $w_D$ denotes a full width at half maximum of a point spread function specific to the X-ray detector.

7. The X-ray Talbot interferometer according to claim 6, wherein a periodic direction of the beam splitter grating and a periodic direction of the analyzer grating match each other.

8. The X-ray Talbot interferometer according to claim 6, wherein m is 1 or 2.

9. The X-ray Talbot interferometer according to claim 6, further comprising the X-ray source.

10. The X-ray Talbot interferometer according to claim 6, further comprising a moving unit configured to cause a relative position of the analyzer grating with respect to the interference pattern to move,
wherein the X-ray detector performs detection before and after the moving unit causes a movement of the relative position to acquire a plurality of detection results at different relative positions of the analyzer grating with respect to the interference pattern.

11. The X-ray Talbot interferometer according to claim 10, wherein the moving unit causes a position of at least one of the beam splitter grating or the analyzer grating to move.

12. The X-ray Talbot interferometer according to claim 10, further comprising a source grating including a plurality of X-ray transmitting portions, configured to allow some of X-rays from an X-ray source to pass therethrough,
wherein the moving unit causes a position of the source grating to move.

13. A X-ray Talbot interferometer system comprising:
the X-ray Talbot interferometer according to claim 6; and
a sample information acquisition unit configured to acquire information on a sample by using information relating to a result of detection performed by the X-ray detector.

14. A X-ray Talbot interferometer system comprising:
the X-ray Talbot interferometer according to claim 10; and
a sample information acquisition unit configured to acquire information on a sample by using information relating to the plurality of detection results.

15. The X-ray Talbot interferometer system according to claim 13, wherein the sample information acquisition unit displays an image or records image information at a data interval having a pixel pitch that is smaller than a pixel pitch of a sampling interval at which the X-ray detector acquires an X-ray intensity distribution.

16. The X-ray Talbot interferometer according to claim 1, further comprising an analyzer grating configured to shield a portion of the interference pattern,
   wherein the X-ray detector detects X-rays from the analyzer grating.

17. The X-ray Talbot interferometer according to claim 16, further comprising a moving unit configured to cause a relative position of the analyzer grating with respect to the interference pattern to move,
   wherein the X-ray detector performs detection before and after the moving unit causes a movement of the relative position to acquire a plurality of detection results at different relative positions of the analyzer grating with respect to the interference pattern.

18. The X-ray Talbot interferometer according to claim 17, wherein the moving unit causes a position of at least one of the beam splitter grating or the analyzer grating to move.

19. The X-ray Talbot interferometer according to claim 17, further comprising a source grating including a plurality of X-ray transmitting portions, configured to allow some of X-rays from an X-ray source to pass therethrough,
   wherein the moving unit causes a position of the source grating to move.

20. A X-ray Talbot interferometer system comprising:
   the X-ray Talbot interferometer according to claim 17; and
   a sample information acquisition unit configured to acquire information on a sample by using information relating to the plurality of detection results.

21. The X-ray Talbot interferometer according to claim 1, further comprising the X-ray source.

22. A X-ray Talbot interferometer system comprising:
   the X-ray Talbot interferometer according to claim 1; and
   a sample information acquisition unit configured to acquire information on a sample by using information relating to a result of detection performed by the X-ray detector.

23. The X-ray Talbot interferometer system according to claim 22, wherein the sample information acquisition unit displays an image or records image information at a data interval having a pixel pitch that is smaller than a pixel pitch of a sampling interval at which the X-ray detector acquires an X-ray intensity distribution.

24. The X-ray Talbot interferometer according to claim 3, further comprising a moving unit configured to cause a relative position of the analyzer grating with respect to the interference pattern to move,
   wherein the X-ray detector performs detection before and after the moving unit causes a movement of the relative position to acquire a plurality of detection results at different relative positions of the analyzer grating with respect to the interference pattern.

25. The X-ray Talbot interferometer according to claim 24, wherein the moving unit causes a position of at least one of the beam splitter grating or the analyzer grating to move.

26. The X-ray Talbot interferometer according to claim 24, further comprising a source grating including a plurality of X-ray transmitting portions, configured to allow some of X-rays from an X-ray source to pass therethrough,
   wherein the moving unit causes a position of the source grating to move.

27. A X-ray Talbot interferometer system comprising:
   the X-ray Talbot interferometer according to claim 24; and
   a sample information acquisition unit configured to acquire information on a sample by using information relating to the plurality of detection results.

28. The X-ray Talbot interferometer according to claim 2, wherein m is 1 or 2.

29. The X-ray Talbot interferometer according to claim 2, further comprising the X-ray source.

30. A X-ray Talbot interferometer system comprising:
   the X-ray Talbot interferometer according to claim 2; and
   a sample information acquisition unit configured to acquire information on a sample by using information relating to a result of detection performed by the X-ray detector.

31. The X-ray Talbot interferometer system according to claim 30, wherein the sample information acquisition unit displays an image or records image information at a data interval having a pixel pitch that is smaller than a pixel pitch of a sampling interval at which the X-ray detector acquires an X-ray intensity distribution.

32. The X-ray Talbot interferometer according to claim 4, wherein m is 1 or 2.

33. The X-ray Talbot interferometer according to claim 4, further comprising the X-ray source.

34. The X-ray Talbot interferometer according to claim 4, further comprising a moving unit configured to cause a relative position of the analyzer grating with respect to the interference pattern to move,
   wherein the X-ray detector performs detection before and after the moving unit causes a movement of the relative position to acquire a plurality of detection results at different relative positions of the analyzer grating with respect to the interference pattern.

35. The X-ray Talbot interferometer according to claim 34, wherein the moving unit causes a position of at least one of the beam splitter grating or the analyzer grating to move.

36. The X-ray Talbot interferometer according to claim 34, further comprising a source grating including a plurality of X-ray transmitting portions, configured to allow some of X-rays from an X-ray source to pass therethrough,
   wherein the moving unit causes a position of the source grating to move.

37. A X-ray Talbot interferometer system comprising:
   the X-ray Talbot interferometer according to claim 34; and
   a sample information acquisition unit configured to acquire information on a sample by using information relating to the plurality of detection results.

38. A X-ray Talbot interferometer system comprising:
   the X-ray Talbot interferometer according to claim 4; and
   a sample information acquisition unit configured to acquire information on a sample by using information relating to a result of detection performed by the X-ray detector.

39. The X-ray Talbot interferometer system according to claim 38, wherein the sample information acquisition unit displays an image or records image information at a data interval having a pixel pitch that is smaller than a pixel pitch of a sampling interval at which the X-ray detector acquires an X-ray intensity distribution.

40. The X-ray Talbot interferometer according to claim 5, wherein a periodic direction of the beam splitter grating and a periodic direction of the analyzer grating match each other.

41. The X-ray Talbot interferometer according to claim 5, further comprising the X-ray source.

42. The X-ray Talbot interferometer according to claim 5, further comprising a moving unit configured to cause a relative position of the analyzer grating with respect to the interference pattern to move,
wherein the X-ray detector performs detection before and after the moving unit causes a movement of the relative position to acquire a plurality of detection results at different relative positions of the analyzer grating with respect to the interference pattern.

43. The X-ray Talbot interferometer according to claim 42, wherein the moving unit causes a position of at least one of the beam splitter grating or the analyzer grating to move.

44. The X-ray Talbot interferometer according to claim 42, further comprising a source grating including a plurality of X-ray transmitting portions, configured to allow some of X-rays from an X-ray source to pass therethrough,
wherein the moving unit causes a position of the source grating to move.

45. A X-ray Talbot interferometer system comprising:
the X-ray Talbot interferometer according to claim 42; and
a sample information acquisition unit configured to acquire information on a sample by using information relating to the plurality of detection results.

46. A X-ray Talbot interferometer system comprising:
the X-ray Talbot interferometer according to claim 5; and
a sample information acquisition unit configured to acquire information on a sample by using information relating to a result of detection performed by the X-ray detector.

47. The X-ray Talbot interferometer system according to claim 46, wherein the sample information acquisition unit displays an image or records image information at a data interval having a pixel pitch that is smaller than a pixel pitch of a sampling interval at which the X-ray detector acquires an X-ray intensity distribution.

* * * * *